US012594675B2

(12) United States Patent
Gao et al.

(10) Patent No.: US 12,594,675 B2
(45) Date of Patent: Apr. 7, 2026

(54) SURGICAL ROBOT, METHOD FOR GUIDING SURGICAL ARM TO MOVE THEREOF, AND COMPUTER READABLE STORAGE MEDIUM THEREOF

(71) Applicant: Shenzhen Edge Medical CO.,Ltd., Guangdong (CN)

(72) Inventors: Yuanqian Gao, Shenzhen (CN); Jianchen Wang, Shenzhen (CN); Guoqiang Ye, Shenzhen (CN)

(73) Assignee: Shenzhen Edge Medical CO., Ltd., Shenzhen (CN)

( * ) Notice: Subject to any disclaimer, the term of this patent is extended or adjusted under 35 U.S.C. 154(b) by 313 days.

(21) Appl. No.: 18/270,848

(22) PCT Filed: Jan. 4, 2022

(86) PCT No.: PCT/CN2022/070065
§ 371 (c)(1),
(2) Date: Jul. 4, 2023

(87) PCT Pub. No.: WO2022/148336
PCT Pub. Date: Jul. 14, 2022

(65) Prior Publication Data
US 2024/0066712 A1 Feb. 29, 2024

(30) Foreign Application Priority Data
Jan. 6, 2021 (CN) .......................... 202110011216.8

(51) Int. Cl.
*B25J 9/16* (2006.01)
*A61B 17/34* (2006.01)
(Continued)

(52) U.S. Cl.
CPC ............. *B25J 9/1697* (2013.01); *A61B 17/34* (2013.01); *A61B 34/30* (2016.02); *G06T 7/593* (2017.01);
(Continued)

(58) Field of Classification Search
USPC ............................... 700/245–264; 606/1, 130
See application file for complete search history.

(56) References Cited

U.S. PATENT DOCUMENTS 7,627,361 B2 * 12/2009 Viswanathan ......... A61B 34/73
600/407
9,980,630 B2 * 5/2018 Larkin ..................... A61B 1/06
(Continued)

FOREIGN PATENT DOCUMENTS

| CN | 109806004 A | 5/2019 | |
| CN | 110464468 A | * 11/2019 | ............. A61B 34/70 |
| CN | 110464468 B | 8/2020 | |

*Primary Examiner* — Jonathan L Sample
(74) *Attorney, Agent, or Firm* — ScienBiziP, P.C.

(57) ABSTRACT

A surgical robot, a method for guiding a surgical arm to move, and a computer readable storage medium thereof. The method includes: acquiring an original position of the operation end effector; determining a target position where the operation end effector is expected to reach; generating a guiding path extended from the original position to the target position according to a vision field of the image end effector; adjusting the operation end effector to move along the guiding path from the original position to the target position. The surgical robot can ensure a safety and a reliability of a surgery.

19 Claims, 15 Drawing Sheets

(51) Int. Cl.

| | | |
|---|---|---|
| *A61B 34/30* | (2016.01) |
| *G06T 7/593* | (2017.01) |
| *G06T 7/70* | (2017.01) |
| *H04N 13/204* | (2018.01) |
| *H04N 23/695* | (2023.01) |

(52) U.S. Cl.

CPC ............. *G06T 7/70* (2017.01); *H04N 13/204*
(2018.05); *H04N 23/695* (2023.01); *G05B*
*2219/39001* (2013.01); *G06T 2207/10012*
(2013.01); *G06T 2207/30004* (2013.01)

(56) References Cited

U.S. PATENT DOCUMENTS

| | | | | |
|---|---|---|---|---|
| 10,905,499 | B2 * | 2/2021 | Rafii-Tari ........... | A61G 13/1295 |
| 11,058,493 | B2 * | 7/2021 | Rafii-Tari ............... | A61B 34/37 |
| 11,129,683 | B2 * | 9/2021 | Steger ................... | A61B 90/00 |
| 11,135,026 | B2 * | 10/2021 | Bono ..................... | A61B 34/25 |
| 11,298,195 | B2 * | 4/2022 | Ye ........................... | A61B 1/042 |
| 2014/0163736 | A1 * | 6/2014 | Azizian .................. | A61B 34/20 |
| | | | | 700/259 |
| 2017/0265774 | A1 * | 9/2017 | Johnson ................. | A61B 34/32 |
| 2018/0042680 | A1 * | 2/2018 | DiMaio ................. | G16H 20/40 |
| 2019/0142520 | A1 * | 5/2019 | VanDyken ............. | A61B 90/37 |
| | | | | 606/1 |
| 2019/0192227 | A1 * | 6/2019 | Shelton, IV ..... | A61B 17/07207 |
| 2019/0206565 | A1 * | 7/2019 | Shelton, IV ........... | A61B 90/90 |
| 2019/0216553 | A1 * | 7/2019 | Bono ..................... | A61B 34/25 |
| 2019/0327394 | A1 * | 10/2019 | Ramirez Luna ....... | A61B 34/77 |
| 2020/0289228 | A1 * | 9/2020 | Denlinger ............. | A61B 6/504 |
| 2020/0352586 | A1 * | 11/2020 | Jinno ..................... | A61B 34/30 |
| 2020/0405403 | A1 * | 12/2020 | Shelton, IV ....... | A61B 17/3421 |
| 2021/0030497 | A1 * | 2/2021 | Daley .................... | A61B 34/76 |
| 2021/0030501 | A1 * | 2/2021 | Eyre ...................... | A61B 34/37 |
| 2021/0045820 | A1 * | 2/2021 | Asadian ................. | A61B 34/35 |
| 2021/0196381 | A1 * | 7/2021 | Eckert ................... | A61B 90/37 |
| 2021/0196382 | A1 * | 7/2021 | Mumaw ................. | G16H 30/20 |
| 2021/0236207 | A1 * | 8/2021 | Stanton ................. | A61B 34/30 |
| 2023/0034112 | A1 * | 2/2023 | Wang .................... | A61B 34/25 |

* cited by examiner

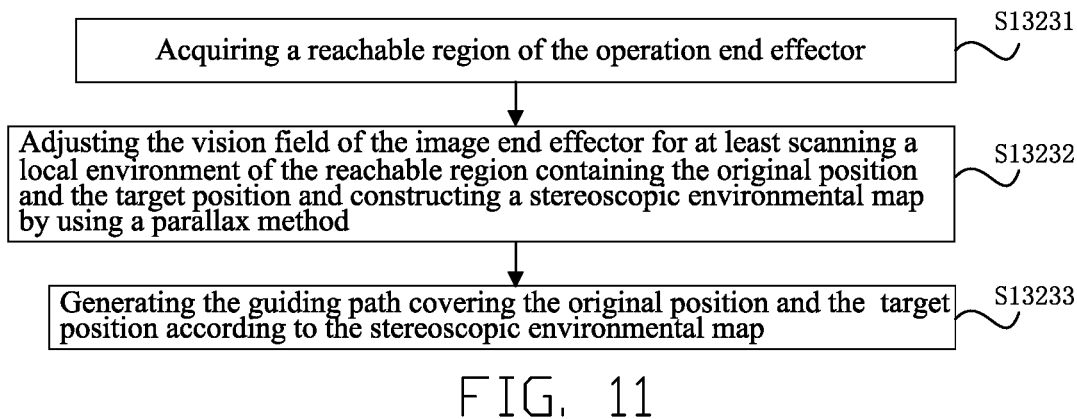

| Acquiring a reachable region of the operation end effector | S13231 |

Adjusting the vision field of the image end effector for at least scanning a local environment of the reachable region containing the original position and the target position and constructing a stereoscopic environmental map by using a parallax method — S13232

Generating the guiding path covering the original position and the target position according to the stereoscopic environmental map — S13233

FIG. 11

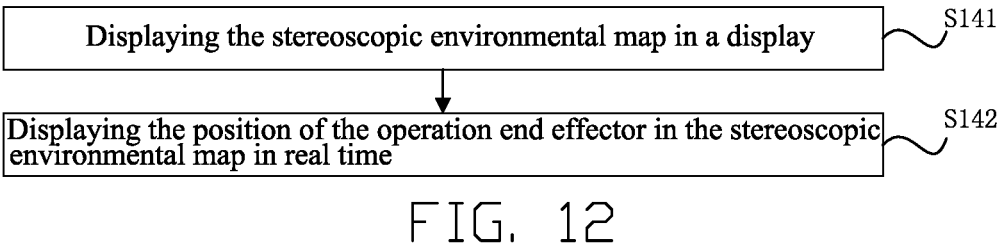

Displaying the stereoscopic environmental map in a display — S141

Displaying the position of the operation end effector in the stereoscopic environmental map in real time — S142

FIG. 12

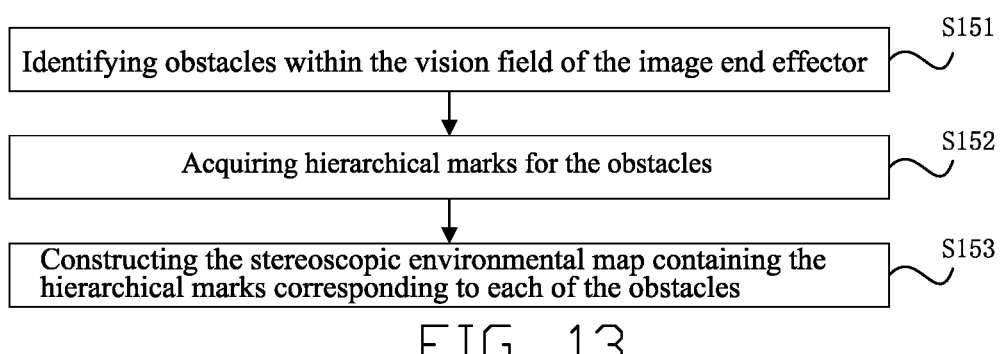

Identifying obstacles within the vision field of the image end effector — S151

Acquiring hierarchical marks for the obstacles — S152

Constructing the stereoscopic environmental map containing the hierarchical marks corresponding to each of the obstacles — S153

FIG. 13

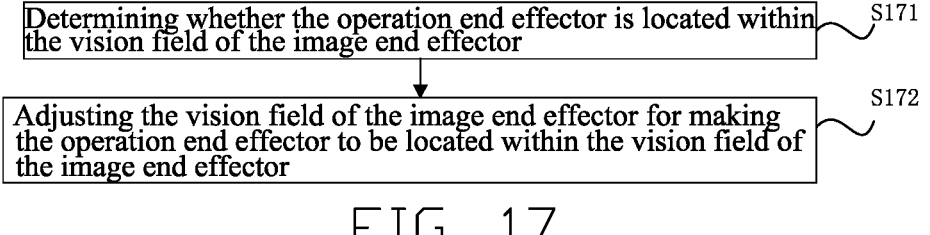

Determining whether the operation end effector is located within the vision field of the image end effector ⟋S171

Adjusting the vision field of the image end effector for making the operation end effector to be located within the vision field of the image end effector ⟋S172

FIG. 17

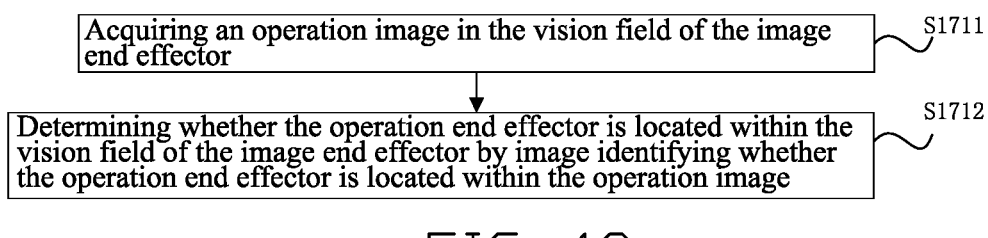

Acquiring an operation image in the vision field of the image end effector ⟋S1711

Determining whether the operation end effector is located within the vision field of the image end effector by image identifying whether the operation end effector is located within the operation image ⟋S1712

FIG. 18

Acquiring a current position of the operation end effector ⟋S1711

Converting the vision field of the image end effector into a position range ⟋S1712'

Determining whether the operation end effector is located withi the vision field of the image end effector by determining whether the current position is located within the position range ⟋S1713'

FIG. 19

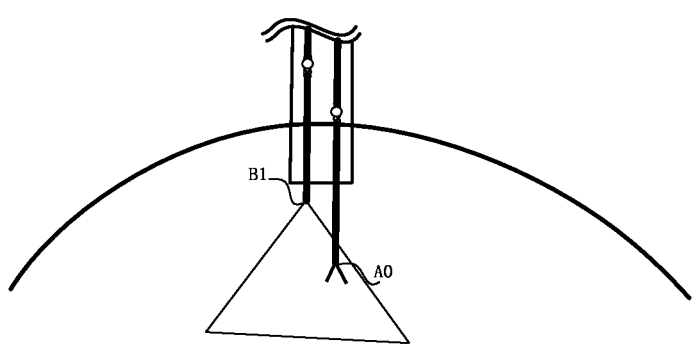
FIG. 26
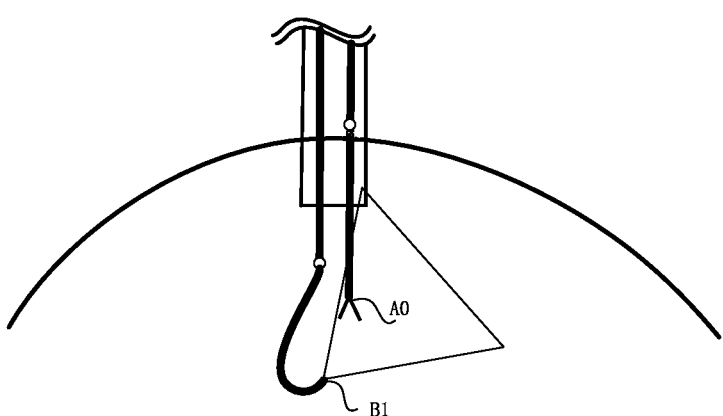
FIG. 27

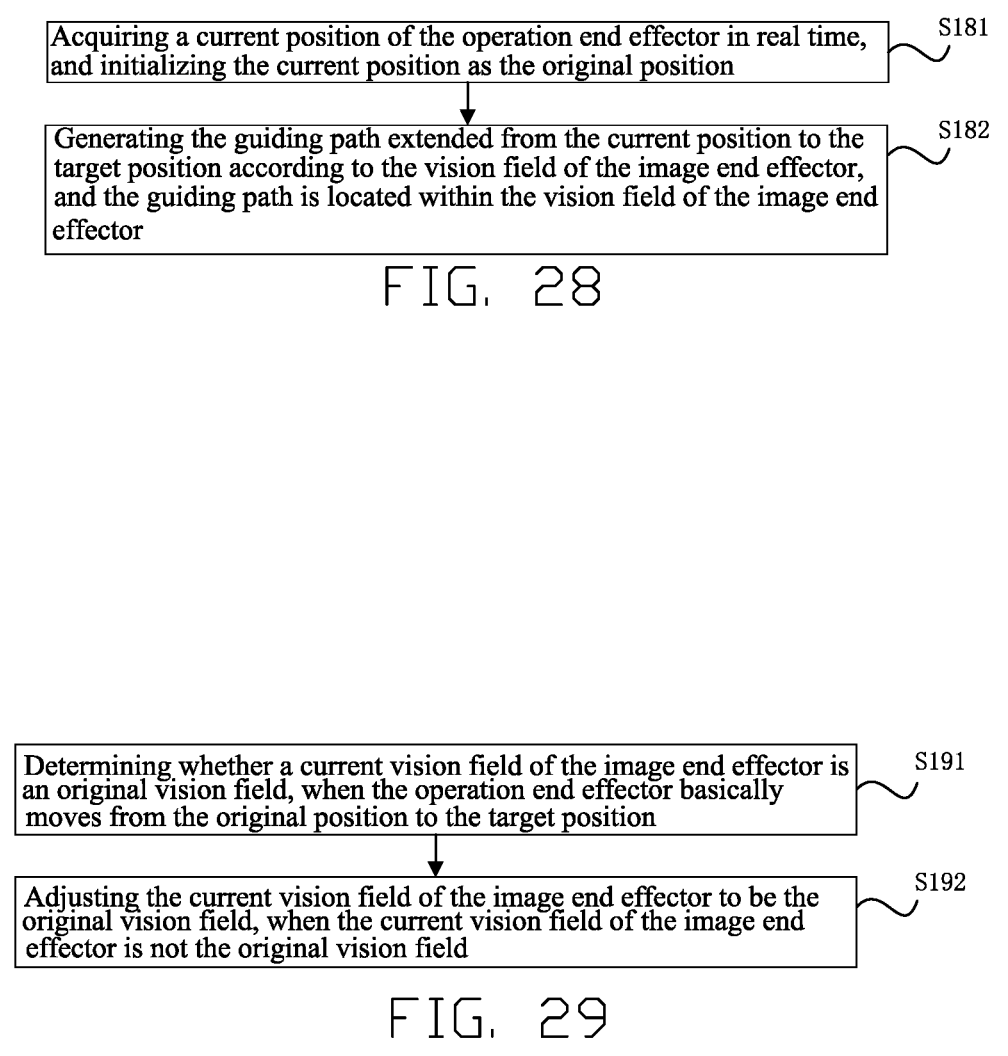

Acquiring a current position of the operation end effector in real time, and initializing the current position as the original position    S181

Generating the guiding path extended from the current position to the target position according to the vision field of the image end effector, and the guiding path is located within the vision field of the image end effector    S182

FIG. 28

Determining whether a current vision field of the image end effector is an original vision field, when the operation end effector basically moves from the original position to the target position    S191

Adjusting the current vision field of the image end effector to be the original vision field, when the current vision field of the image end effector is not the original vision field    S192

FIG. 29

SURGICAL ROBOT, METHOD FOR GUIDING SURGICAL ARM TO MOVE THEREOF, AND COMPUTER READABLE STORAGE MEDIUM THEREOF

The present disclosure claims the priority of the Chinese invention patent disclosure with the invention name "SURGICAL ROBOT, AND SURGICAL ARM MOVEMENT GUIDING METHOD THEREOF AND CONTROL DEVICE THEREOF" submitted to the China Patent Office on Jan. 6, 2021, application No. 202110011216.8, and the whole content of which is hereby incorporated by reference.

TECHNICAL FIELD

The subject matter herein generally relates to medical devices, in particular to a surgical robot, a method for guiding a surgical arm to move, and a computer readable storage medium thereof.

BACKGROUND

Minimally invasive surgery refers to a surgical method of performing a procedure in a human body cavity using modern medical effectors such as laparoscopes, thoracoscopes, and so on. Compared with traditional surgery modes, minimally invasive surgery has advantages of being in little trauma, little pain, fast recovery, and the like.

With advances in science and technology, minimally invasive surgical technologies are increasingly mature and widely used. Surgical robots usually include a master console and a slave operating device, the slave operating device includes a plurality of operating arms, each of the plurality of operating arms includes a camera arm having image end effector and a surgical arm having operation end effector. The master console includes a display and a handle. The doctor operates the handle to control the movement of the camera arm or the surgical arm under a vision field provided by the camera arm on the display.

Generally, the movement of the camera arm itself and the movement of the surgical arm under the vision field of the camera arm may be recognized to be safe. However, during some operation processes, it is impossible to avoid the situation of the surgical arm being moved outside the vision field of the camera arm, for example, a condition of inserting the surgical arm into an abdominal cavity of a patient or extracting the surgical arm from the abdominal cavity of the patient, while inserting or extracting the surgical arm, a blind insertion is usually done through an experience of the doctor. Due to different experiences to the doctors and different body conditions of the patient, an accident situation is easily generated while operating according to the experience. Thus, it is not safe, it is expected to reduce or avoid an operation of moving the surgical arm outside the vision field of the camera arm.

SUMMARY OF THE DISCLOSURE

Based on this, it is necessary to provide a surgical robot, a computer readable storage medium, a method for guiding a surgical robot to move, and a control device thereof to reduce or avoid the operation end effector of the surgical arm to move outside the vision field of the image end effector of the operating arm, for ensuring a surgical safety.

In one aspect, the present disclosure provides a surgical arm movement guiding method in a surgical robot. A distal of the surgical robot includes a plurality of operating arms.

The operating arms include a camera arm having an image end effector and a surgical arm having an operation end effector. The method includes the following steps: acquiring an original position of the operation end effector; determining a target position where the operation end effector is expected to reach; generating a guiding path extended from the original position to the target position according to a vision field of the image end effector; adjusting the operation end effector to move along the guiding path from the original position to the target position.

Optionally, the step of acquiring the original position of the operation end effector includes: acquiring joint variables of each joint assembly in at least including a first part of the surgical arm; determining the original position by combining with a kinematic model of the first part and each of the joint variables using forward kinematic.

Optionally, the step of determining the target position where the operation end effector is expected to reach includes: acquiring an operation mode inputted; the operation mode includes a first operation mode and a second operation mode, the first operation mode is used to guide the operation end effector to insert into a first target position, the second operation mode is used to guide the operation end effector to withdrawn to a second target position; determining the target position where the operation end effector is expected to reach according to the acquired operation mode.

Optionally, when the acquired operation mode is the first operation mode, the step of determining the target position where the operation end effector is expected to reach according to the acquired operation mode includes: acquiring a target vision field of the image end effector; determining the target position where the operation end effector is expected to reach according to the target vision field.

Optionally, more than two operation end effectors being configured to execute the first operation mode have different target positions.

Optionally, more than two operation end effectors being configured to execute the first operation mode having different target positions, and there is a safe distance between different target positions.

Optionally, the surgical robot includes a trocar, a proximal end of the trocar is connected to a distal end of the surgical robot, and a distal end of the trocar is configured to insert and fix at a notch, the trocar is used to guide the surgical arm to insert into a human body through the notch, when the acquired operation mode is the second operation mode, the step of determining the target position where the operation end effector is expected to reach according to the acquired operation mode includes: acquiring a position of a target point related with the trocar as the target position.

Optionally, the target point related with the trocar as the target position is located on the trocar, or is located on an extended line of an axis of the trocar and at a distal end side of the trocar.

Optionally, there is a safe distance between the image end effector and the target position.

Optionally, the step of generating the guiding path extended from the original position to the target position according to the vision field of the image end effector includes: acquiring a guiding mode inputted, the guiding mode includes a first guiding mode and a second guiding mode, the first guiding mode includes a mode of automatically adjusting the vision field of the image end effector, the second guiding mode includes a mode of manually adjusting the vision field of the image end effector; adjusting the vision field of the image end effector according to the acquired guiding mode and generating the guiding path extended from the original position to the target position.

Optionally, the image end effector is a stereoscopic vision image end effector, when the acquired guiding mode is the first guiding mode, the step of adjusting the vision field of the image end effector according to the acquired guiding mode to generate the guiding path extended from the original position to the target position includes: adjusting the vision field of the image end effector for global scanning an environment and constructing a stereoscopic environmental map by using a parallax method; generating the guiding path covering the original position and the target position according to the stereoscopic environmental map.

Optionally, the image end effector is a stereoscopic vision of image end effector, when the acquired guiding mode is the first guiding mode, the step of adjusting the vision field of the image end effector according to the acquired guiding mode to generate the guiding path extended from the original position to the target position includes: acquiring a reachable region of the vision field of the image end effector; adjusting the vision field of the image end effector for scanning an environment of the reachable region and constructing a stereoscopic environmental map by using a parallax method; generating the guiding path covering the original position and the target position according to the stereoscopic environmental map.

Optionally, before the step of adjusting the vision field of the image end effector for scanning the environment of the reachable region and constructing the stereoscopic environmental map by using the parallax method, the method further includes: determining whether both the original position and the target position are located within the reachable region; when both the original position and the target position are located within the reachable region, entering the step of adjusting the vision field of the image end effector for scanning the environment of the reachable region and constructing the stereoscopic environmental map by using the parallax method.

Optionally, the image end effector is a stereoscopic vision of image end effector, when the acquired guiding mode is the first guiding mode, the step of adjusting the vision field of the image end effector according to the acquired guiding mode to generate the guiding path extended from the original position to the target position includes: acquiring a reachable region of the vision field of the image end effector; adjusting the vision field of the image end effector for at least scanning a local environment of the reachable region containing the original position and the target position and constructing a stereoscopic environmental map by using a parallax method; generating the guiding path covering the original position and the target position according to the stereoscopic environmental map.

Optionally, the step of adjusting the vision field of the image end effector for at least scanning the local environment of the reachable region containing the original position and the target position and constructing the stereoscopic environmental map by using the parallax method includes: adjusting the vision field of the image end effector for scanning the environment of the reachable region and constructing the stereoscopic environmental map by using the parallax method.

Optionally, before the step of generating the guiding path covering the original position and the target position according to the stereoscopic environmental map, the method further includes: determining whether both the original position and the target position are located within the reachable region; when both the original position and the target position are located within the reachable region, entering the step of generating the guiding path covering the original position and the target position according to the stereoscopic environmental map.

Optionally, a start point of the guiding path is the original position and an end point of the guiding path is the target position.

Optionally, the surgical robot includes a display, the method further includes: displaying the stereoscopic environmental map in the display; displaying the position of the operation end effector in the stereoscopic environmental map in real time.

Optionally, the position of the operation end effector is displayed in the stereoscopic environmental map in an icon form.

Optionally, the step of generating the guiding path covering the original position and the target position according to the stereoscopic environmental map includes: planning an anti-collision path according to the stereoscopic environmental map for generating the guiding path covering the original position and the target position.

Optionally, the step of constructing the stereoscopic environmental map includes: identifying obstacles within the vision field of image end effector; acquiring hierarchical marks for the obstacles; constructing the stereoscopic environmental map containing the hierarchical marks corresponding to each of the obstacles.

Optionally, the step of acquiring the hierarchical marks for the obstacles includes: acquiring the hierarchical marks corresponding to the obstacles from a default relationship table according to types of the identified obstacles.

Optionally, the step of acquiring hierarchical marks for the obstacles includes: receiving the inputted hierarchical marks corresponding to the obstacles.

Optionally, the step of generating the guiding path covering the original position and the target position according to the stereoscopic environmental map includes: planning an anti-collision path according to the stereoscopic environmental map and its hierarchical marks corresponding to the obstacles for generating the guiding path covering the original position and the target position.

Optionally, the method further includes: when there is no touch relationship between the guiding path and the obstacles, controlling the operation end effector to move at a first speed, and when there is a touch relationship between the guiding path and the obstacles, controlling the operation end effector to move at a second speed lower than the first speed.

Optionally, the method further includes: when there is no touch relationship between the guiding path and the obstacles, adjusting the vision field of the image end effector for locating the operation end effector and/or the corresponding obstacles within the vision field of the image end effector.

Optionally, the method further includes: acquiring a touch range from the guiding path, the touch range is a section range where the operation end effector and the corresponding obstacles have a touch relationship; adjusting the vision field of the image end effector to move from a start point to an end point of the touch range, and consistently ensuring the operation end effector and/or the corresponding obstacles to be capable of falling within the vision field of the image end effector.

Optionally, the hierarchical marks include two levels of a first hierarchical mark and a second hierarchical mark, the obstacles corresponding to the first hierarchical mark are allowed to be touched, the obstacles corresponding to the second hierarchical mark are forbidden to be touched.

Optionally, the hierarchical marks include three levels of a first hierarchical mark, a second hierarchical mark, and a third hierarchical mark, the obstacles corresponding to the first hierarchical mark are allowed to be passed through and touched, the obstacles corresponding to the second hierarchical mark are merely allowed to be touched, the obstacles corresponding to the third hierarchical mark are forbidden to be touched.

Optionally, each of the obstacles also are correspondingly marked with properties information, the properties information includes a destructible first properties information being and an indestructible second properties information.

Optionally, the method further includes: when there is a touch relationship between the guiding path and the obstacles, controlling the operation end effector to pass through the obstacles by a corresponding passing manner according to the hierarchical marks corresponding to the obstacles, the properties information, and the type of the operation end effector.

Optionally, before the step of controlling the operation end effector to pass through the obstacles in the corresponding passing manner according to the hierarchical marks corresponding to the obstacles, the properties information, and the type of the operation end effector, the method further includes: acquiring the hierarchical marks of the obstacles; acquiring the type of the operation end effector; determining the passing manner of the operation end effector for passing through the obstacles according to the hierarchical marks of the obstacles, the properties information, and the type of the operation end effector.

Optionally, in the step of determining the passing manner of the operation end effector for passing through the obstacles according to the hierarchical marks of the obstacles and the type of the operation end effector, under a situation of the obstacle having a first hierarchical mark and a first properties information and the operation end effector having a type of destructible function, determining the passing manner for passing through the obstacles to be a passing manner of damaging the obstacle for passing the obstacles.

Optionally, in the step of controlling the operation end effector to pass through the obstacles by the corresponding passing manner according to the hierarchical marks corresponding to the obstacles and the type of the operation end effector, turning on a destructible function of the operation end effector when the operation end effector arrives at the obstacle, and turning off the destructible function of the operation end effector when the operation end effector leaves the obstacle.

Optionally, in the step of determining the passing manner of the operation end effector for passing through the obstacles according to the hierarchical marks of the obstacles and the type of the operation end effector, under the situation of the obstacle having the first hierarchical mark, the second hierarchical mark, and/or the second properties information, and/or the operation end effector having the type of indestructible function, determining the passing manner for passing through the obstacles to be a passing manner of resisting against the obstacle for passing through the obstacles.

Optionally, when the acquired guiding mode is the second guiding mode, before the step of generating the guiding path extended from the original position to the target position according to the vision field of the image end effector, the method further includes: determining whether the operation end effector is located within the vision field of the image end effector; when the operation end effector is not located within the vision field of the image end effector, adjusting the vision field of the image end effector for making the operation end effector to be located within the vision field of the image end effector; when the operation end effector is located within the vision field of the image end effector, generating the guiding path extended from the original position to the target position according to the vision field of the image end effector.

Optionally, the step of determining whether the operation end effector is located within the vision field of the image end effector includes: acquiring an operation image within the vision field of the image end effector; determining whether the operation end effector is located within the vision field of the image end effector by identifying whether the operation end effector is located within the operation image by the image identifying.

Optionally, the step of determining whether the operation end effector is located within the vision field of the image end effector includes: acquiring a current position of the operation end effector; converting the vision field of the image end effector into a position range; determining whether the operation end effector is located within the vision field of the image end effector for determining whether the current position is located within the position range.

Optionally, the step of adjusting the vision filed of the image end effector for making the operation end effector to be located within the vision field of the image end effector includes: acquiring a current position of the operation end effector; adjusting the vision field of the image end effector for making the operation end effector to be located within the vision field of the image end effector by changing camera parameters of the image end effector according to the current position of the operation end effector, the camera parameters include a field angle and/or a depth of field.

Optionally, the step of adjusting the vision filed of the image end effector for making the operation end effector to be located within the vision field of the image end effector includes: acquiring a current position of the operation end effector, adjusting the vision field of the image end effector for making the operation end effector to be located within the vision field of the image end effector by changing a pose of the image end effector according to the current position of the operation end effector, the pose includes a position and/or an orientation.

Optionally, the step of generating the guiding path extended from the original position to the target position according to the vision field of the image end effector includes: acquiring a current position of the operation end effector in real time, initializing the current position as the original position; generating the guiding path extended from the current position to the target position according to the vision field of the image end effector, and the guiding path is located within the vision field of the image end effector.

Optionally, the step of generating the guiding path extended from the original position to the target position according to the vision field of the image end effector includes: planning an anti-collision path according to the vision field of the image end effector for generating the guiding path extended from the current position to the target position.

Optionally, the method further includes: constraining the adjustment to the vision filed of the image end effector consistently to be under a condition of the operation end effector to be located within the vision field of the image end effector.

Optionally, the vision fields of the image end effector in adjacent time points include a first vision field and a second vision field, there is an overlapped region between the first vision field and the second vision field, limiting the operation end effector to move to the target position by passing through the overlapped region.

Optionally, the method further includes: constraining the vision field of the image end effector to only move towards to a direction of the target position.

Optionally, the method further includes: forbidding the operation end effector to be moved when the operation end effector is not located within the vision field of the image end effector.

Optionally, the method further includes: detecting whether a start instruction is acquired; when the start instruction is acquired, determining whether the operation end effector is located within the vision field of the image end effector.

Optionally, the surgical robot includes a power mechanism for mounting and driving the operating arm, the start instruction is being triggered and generated when the operating arm is mounted on the power mechanism.

Optionally, the method further includes: when the operation end effector basically moves from the original position to the target position, determining whether a current vision field of the image end effector is an original vision field, the original vision field means the vision field of the image end effector at a previous time point before being first adjusted; when the current vision field of the image end effector is not the original vision field, adjusting the current vision field of the image end effector to be the original vision field.

Optionally, before the step of adjusting the operation end effector to move along the guiding path from the original position to the target position, the method further includes: acquiring and recording camera parameters and a pose corresponding to the original vision field, the step of adjusting the current vision field of the image end effector to be the original vision field includes: directly restoring the current vision field of the image end effector to the original vision field according to the recorded camera parameters and the pose corresponding to the original vision field.

In another aspect, the present disclosure provides a computer readable storage medium, the computer readable storage medium stores computer programs, the computer programs are configured to achieve loading and executing the controlling method of any embodiments as mentioned above.

In another aspect, the present disclosure provides a control device of surgical robot, which includes: a storage medium, configured to store computer programs; and a processor, configured to load and execute the computer programs; the computer programs are configured to achieve loading and executing the controlling method of any embodiments as mentioned above.

In another aspect, the present disclosure provides a surgical robot, which includes operating arms, the operating arms include a camera arm having an image end effector and a surgical arm having an operation end effector; and a controller, the controller is coupled with the operating arm and is configured to implement the controlling method of any embodiments as mentioned above.

The surgical robot, the computer readable storage medium, the method for guiding the surgical arm to move, and the control device thereof of the present disclosure has the following beneficial effects:

By generating the guiding path extended from the original position of the operation end effector to the target position using the vision field provided by the image end effector of the camera arm, guiding the operation end effector to move from the original position to the target position using the guiding path, due to the guiding path being generated based on the vision field, a safety and a reliability of the surgical can be ensured.

BRIEF DESCRIPTION OF THE FIGURES

FIGS. 5-14 are respectively flowcharts illustrating a method of guiding the surgical arm of the surgical robot to move according to an embodiment;

FIGS. 17-21 are respectively flowcharts illustrating a method of guiding the surgical arm of the surgical robot to move according to an embodiment;

FIGS. 22-27 are schematic diagram views of guiding states of the operation end effector of the operating arm according to an embodiment;

FIGS. 28-29 are respectively flowcharts illustrating a method of guiding the surgical arm of the surgical robot to move according to an embodiment;

DETAILED DESCRIPTION

For ease of understanding of the present disclosure, the present disclosure will be described more fully hereinafter with reference to the associated drawings. Preferred embodiments of the present disclosure are set forth in the accompanying drawings. This disclosure may, however, be embodied in many different forms and is not limited to the embodiments described herein. Rather, these embodiments are provided for the purpose of providing a more thorough and thorough understanding of the disclosure of the present disclosure.

It should be noted that when an element is referred to as being "disposed on" another element, it may be directly on the other element or intervening elements may also be present. When an element is considered to be "connected" to another element, it may be directly connected to another element or intervening elements may be present at the same time. When an element is considered to be "coupled" to another element, it may be directly coupled to another element or intervening elements may be present at the same time. As used herein, the terms "vertical", "horizontal", "left", "right" and the like are intended for purpose of illustration only and are not intended to be limiting. As used herein, the terms "distal end" and "proximal end" are common terms in the art of interventional medical devices, where "distal end" refers to the end far away from the operator during the surgical procedure, and the "proximal end" refers to the end close to the operator during the surgical procedure.

Unless defined otherwise, all technical and scientific terms used herein have the same meaning as commonly understood by one of ordinary skill in the art. The terminology used herein is for the purpose of describing particular embodiments only and is not intended to be limiting of the invention. As used herein, the term "and/or" includes all combinations of one or more of the associated listed items.

Figure 1:
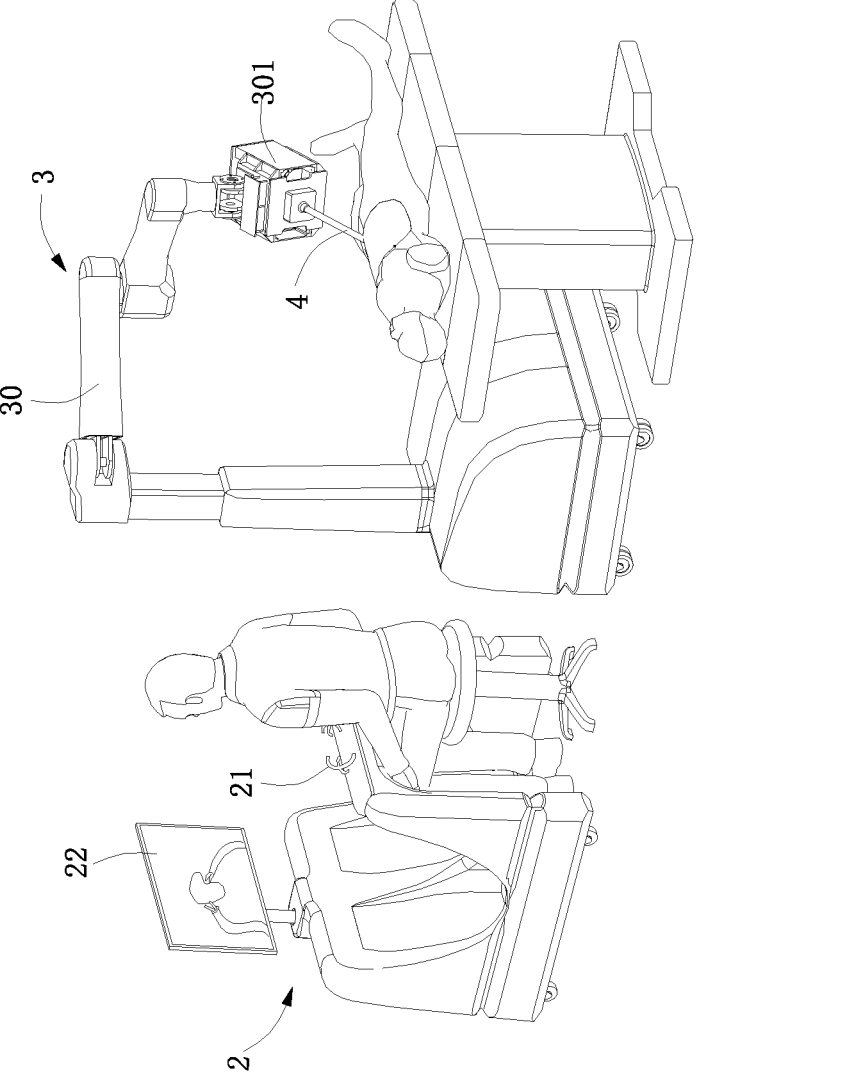
FIG. 1 is a schematic diagram view of a structure of a surgical robot according to an embodiment of the present disclosure.
Figure 2:
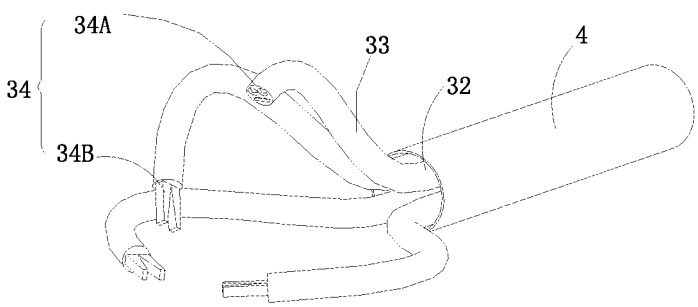
FIG. 2 is a partial schematic diagram of the structure of the surgical robot shown in FIG. 1.

As shown in FIGS. 1 and 2, which are a schematic structural view of a surgical robot according to an embodiment of the present disclosure and a schematic partial view, respectively.

The surgical robot includes a master console 2 and a slave operation device 3 controlled by the master console 2. The master console 2 includes a motion input device 21 and a display 22. The doctor can send a control command to the slave operation device 3 by operating the motion input device 21, for making the slave operation device 3 to perform corresponding operation according to the control command through operating the motion input device 21 by the doctor, and observes the surgical field through the display 22. The slave operation device 3 includes a driving arm, the driving arm includes a mechanical arm 30 and more than one operating arms 31 removably mountable on a distal end of the mechanical arm 30. The mechanical arm 30 includes a base and a connection assembly which are connected in turn. The connection assembly includes a plurality of joint assemblies. The operating arm 31 includes a linkage 32, a connecting assembly 33, and an end effector 34 which are connected in turn, wherein the connecting assembly 33 includes a plurality of joint assemblies, an orientation of the end effector 34 is adjusted by adjusting the joint assemblies of the operating arm 31; the end effector 34 includes an image end effector 34A and an operation end effector 34B. The image end effector 34A is used to capture images in a vision filed, the display 22 is used to display the images. The operation end effector 34B is used to execute surgical operations, such as cutting or suturing. The present disclosure sets the operating arm having the image end effector 34A as a camera arm 31A, and the operating arm having the operation end effector 34B as a surgical arm 31B.

The surgical robot as shown in FIG. 1 is a single-port surgical robot, each of the operating arms 31 inserts into a body of a patient through a same trocar 4 mounted on a distal end of the mechanical arm 30. In the single-port surgical robot, the doctor generally only controls the operating arm 31 for completing basic surgical operations. In this case, the operating arm 31 of the single-port surgical robot should have position-related degree of freedom (that is, degrees of freedom for determining position) and an orientation-related degree of freedom (that is, degrees of freedom for determining orientation) for achieving a pose change in a certain range, for example, the operating arm 31 has a horizontal moving degree of freedom x, a vertical moving degree of freedom y, a rotation degree of freedom α, a pitch degree of freedom β, and a yaw degree of freedom γ, the operating arm 31 also can achieve a back and forth moving degree of freedom z under the driving of the joint assemblies in the distal end of the mechanical arm 30, which is the power mechanism 301. Besides, in some embodiments, redundancy degree of freedom can be set for the operating arm 31 for achieving possibility of more functions, for example, under a premise of achieving above 6 degrees of freedom, one, two, even more degrees of freedom are extra set. For example, the power mechanism 301 has a guiding rail and a power portion slidably disposed on the guiding rail, the operating arm 31 is removably mounted on the power portion, on the one hand, the power portion slides on the guiding rail for providing the back and forth moving degree of freedom z to the operating arm 31, and on the other hand, the power portion provides power to the joint assemblies of the operating arm 31 for achieving the other five degrees of freedom (which is [x, y, α, β, γ]).

The surgical robot also includes a controller. The controller can be integrated into the master console 2 or the slave operation device 3. Certainly, the controller also can be set independently of the master console 2 and the slave operation device 3, and the controller can be deployed locally or in the cloud. The controller can include more than one processor.

The surgical robot also includes an input device. The input device can be integrated into the master console 2. The input device also can be integrated into the slave operation device 3. Certainly, the input device also can be set independently of the master console 2 and the slave operation device 3. The input device can be a mouse, a keyboard, a voice input device, a touch screen, for example. In one embodiment, using the touch screen as the input device, the touch screen can be set on an armrest of the master console 2, for example.

The operating arm 31 also includes sensors for sensing the joint variables of the joint assembly. The sensors include angle transducers for sensing rotation motion of the joint assembly and displacement transducers for sensing linear motion of the joint assembly, specifically suitable sensors can be set according to the type of the joint assembly.

The controller is coupled to these sensors and is coupled to the input device and the display 22.

Figure 3:
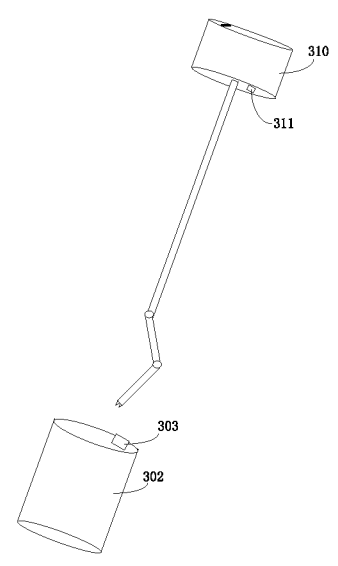
FIG. 3 is a flowchart of a controlling method of a surgical robot according to an embodiment.

Exemplary, as shown in FIG. 3, a resisting surface of a driving box 310 of the operation arm 31 resisting with the power portion 302 of the power mechanism 301 mounts a storage unit 311, correspondingly a resting surface of the power portion 302 resisting with the driving box 310 mounts a reading unit 303 matched with the storage unit 311, the reading unit 303 is coupled with the controller, when the operating arm 31 is mounted on the power portion 302, the reading unit 303 communicates with the storage unit 311, the reading unit 303 reads related information from the storage unit 311. The storage unit 311 can be a storage memory or an electronic tag, for example. The storage unit stores a type of the operating arm, portions of the operating arm capable of being configured to be a target portion, kinematic model of the operating arm, for example. For example, camera parameters are further stored in the storage unit 311 of the camera arm 31A.

Figure 4:
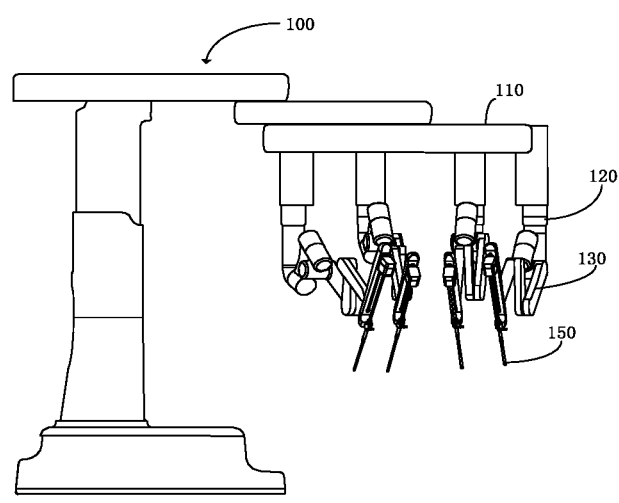
FIG. 4 is a schematic diagram view of a structure of an operating arm and a power portion of a surgical robot.

As shown in FIG. 4, FIG. 4 is a schematic structural view of a structure of the surgical robot according to an embodiment of the present disclosure. More specifically, FIG. 4 shows a structure of multi-port surgical robot according to an embodiment. A difference between the multi-port surgical robot shown in FIG. 4 and the single-port surgical robot as shown in FIG. 1 is the difference between the slave operation devices of therebetween. The driving arm of the slave operation device in the multi-port surgical robot includes a mechanism arm 110, an adjusting arm 120, a manipulator 130, and an operating arm 150, which are connected in turn. The number of the manipulators 130 and the number of the operating arms 150 are same and are more than two, such as four, a distal end of the mechanism arm 110 has an orienting platform, proximal ends of the adjusting arms 120 are connected to the orienting platform, a distal end of the manipulator 130 is connected with a proximal end of the adjusting arm 120. The manipulator 130 is removably connected with the operating arm 150, the manipulator 130 has a plurality of joint assemblies. Each of the manipulators 130 has a power mechanism, the operating arm 150 is mounted on the power mechanism and is driven by the power mechanism. In the multi-port surgical robot, different operating arms 150 are inserted into the body of the patient through different trocars, the operating arms 150 of the multi-port surgical robot be compared with the operating arm 31 of the single-port surgical robot generally has less degree of freedom, usually, the operating arm 150 only has an orientation-related degree of freedom (that is, degrees of freedom for determining orientation), an orientation change of the operating arm 150 generally generates effect on position, but it can be omitted under some scenes because it has less affected. The position change of the operating arm 150 generally is achieved by the assistance of the manipulator 130, the pose is changed because of the coordinative movement of the manipulator 130 and the operating arm 150, which can be recognized as a manipulator assembly, being equivalent to the operating arm 31 of the single-port surgical robot.

According to configurations, a motion input device 21 can input pose instructions including position instructions and orientation instructions for controlling a pose change of the distal end of the first part in the driving arm. The distal end of the first part generally is the end effector, besides, the distal end of the first part also is one joint assembly connected with the end effector, a pose change of the end effector is generally consistent with the pose change of the joint assembly.

In the surgical robot as shown in FIG. 1, the driving arm includes the mechanical arm and the operating arm, the proximal end of the operating arm is mounted on the distal end of the mechanical arm, and the end effector is mounted on the distal end of the operating arm. According to the configuration, the first part can be configured as the operating arm; or the first part can be configured as a whole of the mechanical arm and the operating arm.

And correspondingly in the surgical robot as shown in FIG. 4, the driving arm includes the mechanical arm, the adjusting arm, the manipulator, and the operating arm, the proximal end of the adjusting arm is mounted on the distal end of the mechanical arm, the proximal end of the manipulator is mounted on the distal end of the adjusting arm, the proximal end of the operating arm is mounted on the distal end of the manipulator, the end effector is mounted on the distal end of the operating arm. According to the configuration, the first part can be configured as the operating arm; or the first part can be configured as a whole of the mechanical arm and the operating arm; or the first part can be configured as a whole of the mechanical arm, the adjusting arm, the manipulator, and the operating arm.

It is understood that, no matter the single-port surgical robot as shown in FIG. 1 or the multi-port surgical robot as shown in FIG. 4, the mechanical arm is generally used to adjust pose of the end effector on a large scale, the operating arm is used to finely adjust pose of the end effector, for example, before the surgery the position is positioned by the mechanical arm, and the like, in the surgery the surgery is performed by controlling the operating arm. Certainly, in some embodiments, specific function can be achieved by combining the mechanical arm, the operating arm, and the corresponding arm structures to move in concert together. According to the configuration, more than one end effectors can be configured as controlled end effectors for receiving the controlling of the motion input device.

Figure 5:
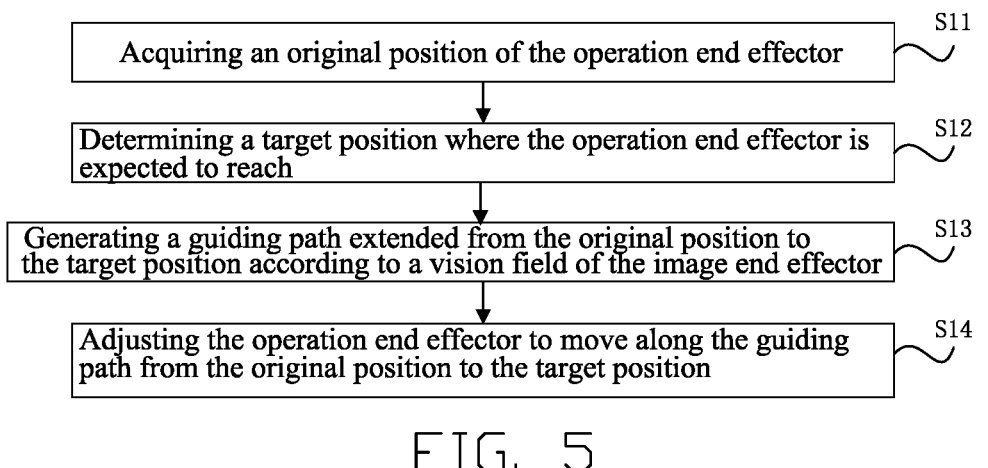

In one embodiment, the present disclosure provides a method of guiding the surgical arm to move in the surgical robot, the method can be executed by the controller, and is suitable to several types of surgical robots for using. As shown in FIG. 5, the method includes the following steps:

In block S11, acquiring an original position of the operation end effector.

For example, joint variables of each joint assembly at least including the surgical arm in the first part can be firstly acquired, then the original position is determined by combining a kinematic model of the first part and each of the joint variables using forward kinematic. For example, in a regular control mode of the single-port surgical robot, the original position of the operation end effector can be only determined by the joint variables of each joint assembly in the surgical arm and the kinematic model. For example, in a regular control mode of the single-port surgical robot, the original position of the operation end effector can be determined by the joint variables of each joint assembly in the surgical arm and the manipulator and the kinematic model.

In block S12, determining a target position where the operation end effector is expected to reach.

Positions and orientations of different objects related in the present disclosure are described based on a same reference coordinate system. These different objects include the image end effector of the camera arm and the operation end effector of the operating arm, but not being limited. The reference coordinate system includes a base coordinate system of the surgical robot, but not being limited, for example, also can be other reference coordinate system by converting based on the base coordinate system, such as the coordinate system of the master console.

The target position can be a position located within the vision field of the image end effector, also can be a position not being located within the vision field of the image end effector, which can be determined according to a requirement in a process of the surgery in detail.

In block S13, generating a guiding path extended from the original position to the target position according to a vision field of the image end effector.

According to a covering range of the vision field of the image end effector, the guiding path can be a whole or a part of a full path from the original position to the target position. The original position and the target position are two interval points on the guiding path.

In block S14, adjusting the operation end effector to move along the guiding path from the original position to the target position.

In the above blocks S11-S14, the concerned related position of the operation end effector can be a local of the operation end effector for example, such as the related positions of one or more points on a tip end, a middle portion, or a tail end of the operation end effector, or the related position of the whole of the operation end effector.

When the guiding path is the whole of the full path from the original position to the target position, the operation end effector can be directly and automatically guides from the original position to the target position. When the guiding path is a part of the full path from the original position to the target position, the operation end effector can be automatically guides from the original position towards the target position for closing to the target position. The principle is as follows:

The guiding path is dispersed into a plurality of sub-target positions, then the corresponding sub-target positions for achieving the joint variables of each joint assembly including the first part of the surgical arm are solved through an inverse kinematic, each of the joint assemblies including in the first part of the surgical arm is controlled to be move to the corresponding joint variables, that is the operation end effector being guided to arrive the corresponding sub-target positions.

According to the above blocks S11-S14, that is the generated guiding path extended from the original position of the operation end effector to the target position using the vision field provided by the image end effector in the camera arm, further the operation end effector is guided to automatically move from the original position to the target position using the guiding path, because the guiding path is generated based on the vision field, thus a safety and a reliability of the surgical can be ensured.

Figure 6:
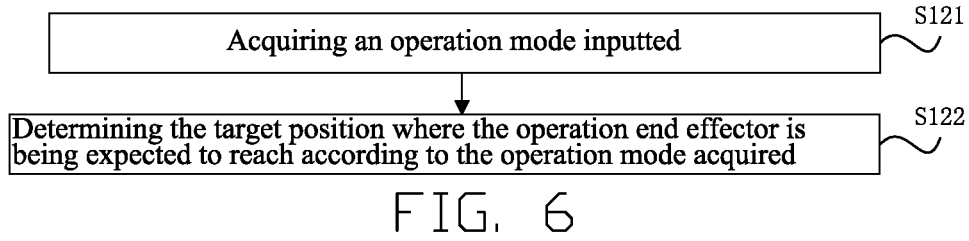

Generally, different operation requirements correspond to different target positions of the operation end effector. In one embodiment, as shown in FIG. 6, the block S12, that is the step of determining the target position where the operation end effector is expected to reach includes:

In block S121, acquiring an operation mode inputted.

The operation mode includes a first operation mode and a second operation mode, but not being limited. For example, the first operation mode is used to guide the operation end effector to insert into the target position, a scene suitable for the first operation mode includes a scene of inserting the operating arm from an outside of the body of the patient into the body of the patient before surgical, but not being limited; the second operation mode is used to guide the operation end effector to withdrawn to the target position, scenes suitable for the second operation mode include the scenes of changing the operating arm in the process of the surgical or withdrawing the operating arm when ending the surgical, but not being limited.

In block S122, determining the target position where the operation end effector is expected to reach according to the operation mode acquired.

Figure 7:
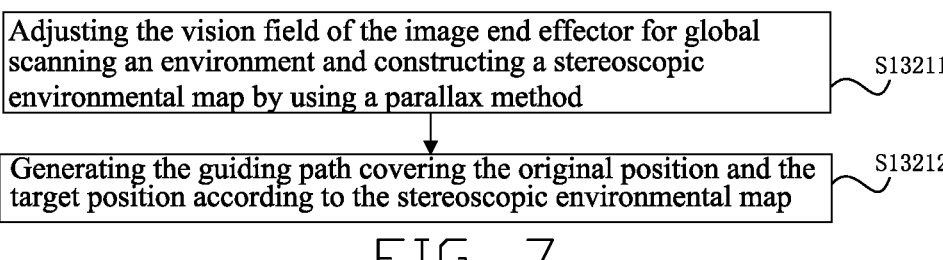

In one embodiment, when the operation mode acquired is the first operation mode, as shown in FIG. 7, the above block S122, that is the step of determining the target position where the operation end effector is expected to reach according to the operation mode acquired includes:

In block S1221, acquiring a target vision field of the image end effector.

The target vision field can be a confirmed vision field as the target vision field, which is a vision field confirmed by a doctor at a time point, for example, the surgical is generally implemented under the target vision field. For example, the doctor generally firstly inserts the camera arm into the body of the patient, the vision field suitable for implementing the surgical is observed and confirmed using the image end effector of the camera arm, after receiving a determining instruction triggered by the doctor, the vision field corresponding to the time point generated the determining instruction serves as the above target vision field.

In block S1222, determining the target position where the operation end effector is expected to reach according to the target vision field.

The target position is a point with a specific position relationship with the target vision field. The target position can be a center of the target vision field for example, or a point being off the center of the target vision field and being intersected with an extended direction of a linage of the operating arm.

In one embodiment, more than two operation end effectors being configured to execute the first operation mode have different target positions, further, there is safe distances between different target positions, for avoiding a collision between the operation end effectors. For example, in these target positions, one of these target positions can be allowed to be a center point of the vision fields, and the rest of these target positions can be specific points besides the center point of the vision fields.

In one embodiment, when there are more than two operation end effectors needed to be guided to the target positions, the operation end effectors generally can be guided one by one, that is, after one of the operation end effectors is guided to arrive at the target position, then a next operation end effector is guided to arrive at the target position, until all of the operation end effectors are guided to arrive at the target position.

The surgical robot includes a trocar. A proximal end of the trocar is removably connected to a distal end of the surgical robot, and a distal end of the trocar is inserted and fixed at a notch. The trocar is used to guide the surgical arm to insert into a human body through the notch. In one embodiment, when the operation mode acquired is the second operation mode, the above block S1222, that is, the step of determining the target position where the operation end effector is expected to reach according to the operation mode acquired is: acquiring a position of a point related with the trocar as the target position. The point related with the trocar as the target position can be located on the trocar, and also can be located on an extended line of an axis of the trocar and at the distal end side of the trocar, the trocar generally includes a cylindrical insert assembly, and the axis generally is a center axis of the insert assembly.

In the above embodiment, there is a safety distance between the image end effector and the target position, for avoiding the collision between the image end effector and the operation end effector.

Figure 8:
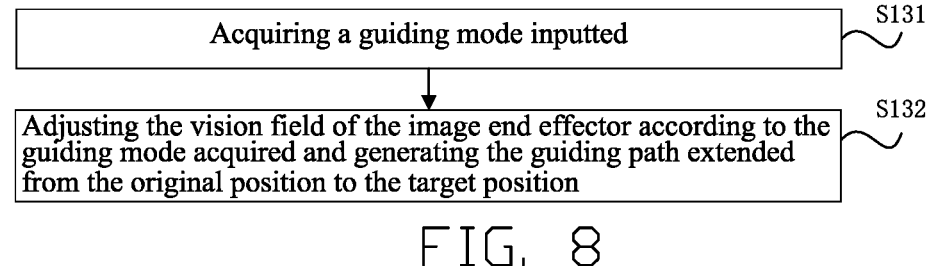

Generally, according to different adjustments of the camera arm, the generating manners of the guiding path are also different. In one embodiment, as shown in FIG. 8, the above block S13, that is the step of generating the guiding path extended from the original position to the target position according to the vision field of the image end effector, includes:

In block S131, acquiring a guiding mode inputted.

The guiding mode includes a first guiding mode and a second guiding mode, the first guiding mode is a mode of automatically adjusting the vision field of the image end effector, and the second guiding mode is a mode of manually adjusting the vision field of the image end effector.

In block S132, adjusting the vision field of the image end effector according to the guiding mode acquired and generating the guiding path extended from the original position to the target position.

When the guiding mode acquired is the first guiding mode, the above block S132 can be implemented in different embodiments. The guiding path is generated according to the vision filed acquired of the stereoscopic vision image end effector, a change of the vision field of the image end effector can be automatic, and also can be manual. Besides, the guiding path is generated using sensing information of an ultrasound sensor or optical sensor. Certainly, they can be combined used. The guiding path being generated by using the vision field acquired by the stereoscopic vision image end effector is used as an example for illustrating. When the guiding mode acquired is the first guiding mode, for example, the following three manners can implement the above block S132.

Embodiment 1

Figure 9:
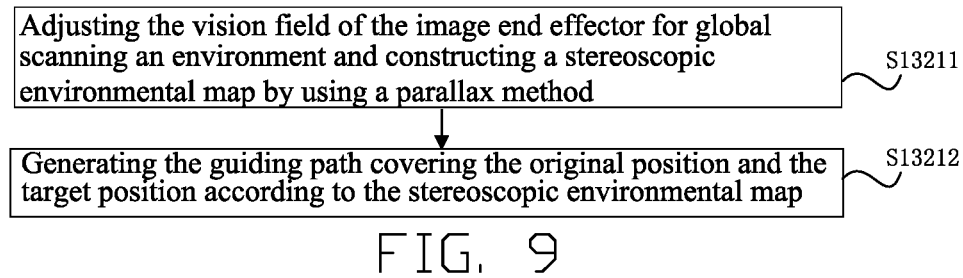

As shown in FIG. 9, the above block S132 can include:

In block S13211, adjusting the vision field of the image end effector for global scanning an environment and constructing a stereoscopic environmental map by using a parallax method.

That is, an environment inside the patient is global scanned. The camera arm is not being limited to move around a telecentric fixed point (that is a remote center of motion, RCM) for achieving the global scanning.

In block S13212, generating the guiding path covering the original position and the target position according to the stereoscopic environmental map.

The guiding path covering the original position and the target position means that the points constituted the guiding path include the original position and the target position.

Embodiment 2

Figure 10:
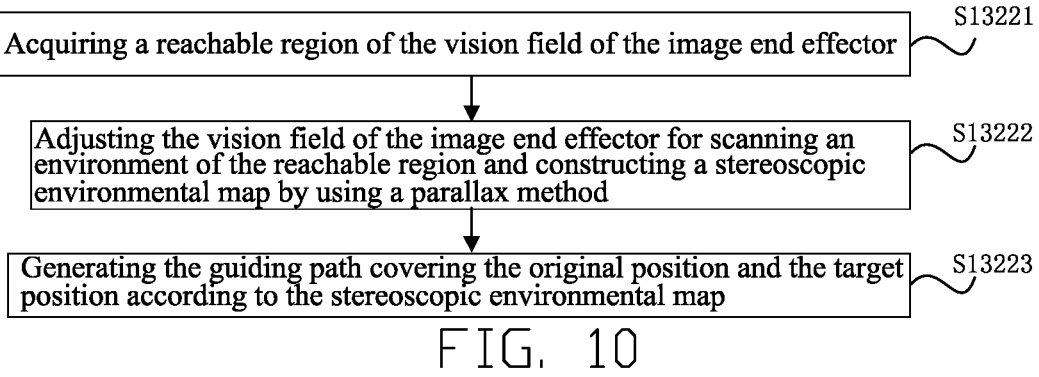

As shown in FIG. 10, the above block S132 can include:

In block S13221, acquiring a reachable region of the vision field of the image end effector.

The reachable region of the vision field of the image end effector is a space set of all vision fields of the image end effector.

In block S13222, adjusting the vision field of the image end effector for scanning an environment of the reachable region and constructing a stereoscopic environmental map by using a parallax method.

The reachable region of the vision field is a reachable region while the camera arm moves around the telecentric fixed point, for example.

In block S13223, generating the guiding path covering the original position and the target position according to the stereoscopic environmental map.

Preferably, before the above block S13222, that is, the step of adjusting the vision field of the image end effector for scanning the environment of the reachable region and constructing the stereoscopic environmental map by using the parallax method, includes: determining whether both the original position and the target position are located within the reachable region. When both the original position and the target position are located within the reachable region, the block S13222 is entered; otherwise, prompting the doctor to adjust the image end effector and/or the operation end effector for satisfying the starting condition.

Embodiment 3

As shown in FIG. 11, the above block S132 can include:

In block S13231, acquiring a reachable region of the operation end effector.

The reachable region of the operation end effector means a reachable motion range of the operation end effector. The reachable region of the operation end effector is a reachable region while the operating arm moves around the telecentric fixed point, for example.

In block S13232, adjusting the vision field of the image end effector for at least scanning a local environment of the reachable region containing the original position and the target position and constructing a stereoscopic environmental map by using a parallax method.

For example, a part of the reachable region containing the original position and the target position is scanned by adjusting the vision field of the image end effector, and the stereoscopic environmental map of the part of the reachable region is constructed by using the parallax method. For another example, the whole reachable region is scanned by adjusting the vision field of the image end effector, and the stereoscopic environmental map of the whole reachable region is constructed by using the parallax method.

In block S13233, generating the guiding path covering the original position and the target position according to the stereoscopic environmental map.

For example, in the example of scanning the whole reachable region by adjusting the vision field of the image end effector and constructing the stereoscopic environmental map of the whole reachable region by using the parallax method, preferably, the method of the present disclosure also can include: determining whether the reachable region of the operation end effector is located within the reachable region of the vision field of the image end effector. When the reachable region of the operation end effector is located within the reachable region of the vision field of the image end effector, the block of adjusting the vision field of the image end effector for scanning the environment of the whole reachable region and constructing the stereoscopic environmental map by using the parallax method is entered; otherwise, prompting the doctor to adjust the image end effector and/or the operation end effector for satisfying the starting condition.

In the above three embodiments, preferably, before the block of generating the guiding path covering the original position and the target position according to the stereoscopic environmental map, the method can further include: determining whether both the original position and the target position are located within the reachable region of the operation end effector. When both the original position and the target position are located within the reachable region of the operation end effector, entering the block of constructing the stereoscopic environmental map or the block of generating the guiding path covering the original position and the target position according to the stereoscopic environmental map, that is, the step of determining can be implemented before the step of constructing the stereoscopic environmental map, also can be implemented before the step of generating the guiding path covering the original position and the target position according to the stereoscopic environmental map; otherwise, the doctor is prompted to adjust the image end effector and/or the operation end effector for satisfying the starting condition. The implemented the determination is designed to determine whether the operation end effector can arrive the target position from the original position, if it fails to arrive, in a requirement of certainly arriving the target position, it is not necessary for continuing implementing. In fact, even if the operation end effector fails to arrive the target position, the guiding path extended form the original position to the target position can be also constructed according to the stereoscopic environmental map, for trying to adjust the operation end effector to move close to the target position.

For example, in the above blocks S13212, S13223, and S13233, which are the blocks of generating the guiding path covering the original position and the target position according to the stereoscopic environmental map, a start point of the guiding path being planned is the original position and an end point of the guiding path is the target position.

In one embodiment, as shown in FIG. 12, the method of the present disclosure also includes:

In block S141, displaying the stereoscopic environmental map in a display.

In block S142, displaying the position of the operation end effector in the stereoscopic environmental map in real time.

For example, the position of the operation end effector is displayed in the stereoscopic environmental map in an icon form. For example, the icon is the icon of the operation end effector, for another example, the icon is a light spot.

By the blocks S141 and S142, it can assist the doctor for acquiring a position relationship between the operation end effector and the environment, such as for acquiring a position relationship between the operation end effector and the obstacles.

In the above blocks S13212, S13223, and S13233, there are a plurality of planning manners for generating the guiding path covering the original position and the target position according to the stereoscopic environmental map, for example, the planned guiding path is a shortest path, for another example, the planned guiding path is a smoothest path. In one embodiment, the blocks can plan an anti-collision path according to the stereoscopic environmental map for generating the guiding path covering the original position and the target position, the method for planning the anti-collision path can include graph search algorithm, RRT algorithm, artificial potential field, but not being limited. Preferably, when there are several guiding paths satisfying with non-collision, constraint condition can be combined for optimizing selecting, such as a best guiding path is selected by combining with the shortest path and/or the smoothest path.

Because the complex environment of the body, if the obstacles in the environment are absolutely untouchable and need to be avoided, it is usually not practicable for a surgical process being manually implemented by the doctor, thus it can be considered for classifying the obstacles by combining actual situation or experiences, for distributing the obstacles being touchable in fact, therefore it is also helpfully in more flexibly planning the guiding path.

In one embodiment, as shown in FIG. 13, the steps of constructing the stereoscopic environmental map in the blocks S13212, S13223, and S13233 also include:

In block S151, identifying obstacles within the vision field of the image end effector.

With the help of neural network, such as convolutional neural network, the obstacles within the vision field are identified. In the present disclosure, these obstacles can be human tissue and organs, also can be object such as an operating arm inserted into an animal.

In block S152, acquiring hierarchical marks for the obstacles.

For example, the hierarchical marks of the obstacles can be automatically acquired from a default relationship table according to the types of the identified obstacles, which are automatically executed. In another example, the hierarchical marks corresponding to the obstacles inputted by the doctor are received, which are manually executed. Certainly, in some scenes, the hierarchical marks can be acquired by combining both, which is helpful in quickly classifying and mutual authentication.

For example, the hierarchical marks can be divided into two levels. Such as, the hierarchical marks include a first hierarchical mark and a second hierarchical mark. The obstacles corresponding to the first hierarchical mark are allowed to be touched by the operation end effector, such as the position of which can be changed under a touch of the operation end effector; the obstacles corresponding to the second hierarchical mark are forbidden to be touched by the operation end effector, which needs to be avoided strictly.

For example, adipose tissue of human body can be set as the first hierarchical mark; important organs of human body can be set as the second hierarchical mark, such as liver, kidney, spleen, stomach, blood vessels, heart, intestinal tract, gall bladder, and other operating arms, but not being limited.

For example, the hierarchical marks can be divided into three levels. Such as, the hierarchical marks include a first hierarchical mark, a second hierarchical mark, and a third hierarchical mark. The obstacles corresponding to the first hierarchical mark are allowed to be directly passed through by the operation end effector, the obstacles corresponding to the second hierarchical mark are allowed to be touched by the operation end effector, the obstacles corresponding to the third hierarchical mark are forbidden to be touched by the operation end effector. The term "directly pass through" includes the meaning of "touch", that is it can be directly passed through, also can be touched. The term of "touch" does not include other meanings. That is, the first to third hierarchical marks are divided according to effects of the obstacles to the path from light to heavy. For example, adipose tissue of human body can be set as the first hierarchical mark; important organs of human body can be set as the second hierarchical mark, such as liver, kidney, spleen, stomach, intestinal tract, but not being limited; the important organs of human body can be set as the third hierarchical mark, such as blood vessels, heart, gall bladder, and other operating arms, but not being limited. The hierarchical marks are examples, which can be defined due to a requirement.

Certainly, the hierarchical marks can be divided into more levels, which is helpful in flexibly planning the anti-collision guiding path.

In block S153, constructing the stereoscopic environmental map containing the hierarchical marks corresponding to each of the obstacles.

For example, the hierarchical mark of each of the obstacles is labeled in a corresponding image attribute of each of the obstacles in the stereoscopic environmental map.

Therefore, the guiding path is reasonably planned by using the stereoscopic environmental map containing the corresponding hierarchical marks of each of the obstacles. In one embodiment, specifically in the above blocks S13212, S13223, and 13233, that is, in the step of generating the guiding path covering the original position and the target position according to the stereoscopic environmental map, planning the anti-collision path according to the stereoscopic environmental map and the hierarchical marks corresponding to the obstacles contained in the stereoscopic environmental map and generating the guiding path covering the original position and the target position.

By comparing with the situation that the obstacles are unable to avoid and the effective guiding path is unable to be planned which are caused by the obstacles without being divided into hierarchical marks while planning the anti-collision guiding path, under a condition of the same stereoscopic environmental map, the obstacles are divided into two levels having the first hierarchical mark and the second hierarchical mark, because the obstacles corresponding to the first hierarchical mark are touchable, thus it is possible to exist an effective guiding path, further, the obstacles are divided into three levels having the first hierarchical mark, the second hierarchical mark, and the third hierarchical mark, because the obstacles corresponding to the first hierarchical mark can be directly pass through, and the obstacles corresponding to the second hierarchical mark are touchable, thus a probability of existence of an effective guiding path is higher. Therefore, the higher levels of reasonable hierarchical marks are, in most cases, a probability of planning an effective and anti-collision guiding path will be higher.

In some embodiments, a same obstacle can only have one manner of hierarchical division. For example, the obstacles are recommended to not divide into different hierarchical marks for planning the anti-collision guiding path, if the guiding path is existed, the guiding of the operation end effector is the most reliable and safe, if the guiding path is not existed, it can be considered for dividing the obstacles into different hierarchical marks for planning the anti-collision guiding path. For example, when there only two above levels in division, the obstacles are divided into the two levels of the first hierarchical mark (touchable) and the second hierarchical mark (untouchable) for planning the anti-collision guiding path, in one hand, the probability of planning a reasonable guiding path is improved, and in another hand, a requirement of reliably and safely guiding the operation end effector is satisfied. For example, when there only three above levels in division, the obstacles are divided into the three levels of the first hierarchical mark (capable of passing through), the second hierarchical mark (touchable), and the third hierarchical mark (untouchable) for planning the anti-collision guiding path, the probability of planning a reasonable guiding path is further improved, and a requirement of reliably and safely guiding the operation end effector is also satisfied.

In some embodiments, a same obstacle can have different manners of hierarchical divisions. For example, the obstacles are recommended to not divide into different hierarchical marks for planning the anti-collision guiding path, if the guiding path is existed, the guiding of the operation end effector is the most reliable and safe, in the case of the existence of the guiding path, the operation end effector is controlled to move at a first speed. The obstacles are not divided into different hierarchical marks for planning the anti-collision guiding path, and the guiding path is not existed, it can be considered for dividing the obstacles into different hierarchical marks for planning the anti-collision guiding path. For example, when the manners of the division have both the above two levels and the above three levels, the obstacles are firstly divided into the two levels of the first hierarchical mark (touchable) and the second hierarchical mark (untouchable) for planning the anti-collision guiding path, if it is possible to plan the reasonable guiding path under this level, the guiding path is adopted to guide the operation end effector to move, in case of the existence of the guiding path, the operation end effector is controlled to move at a second speed being lower than the first speed; if it is not possible to plan the reasonable guiding path under this level, the obstacles are further divided into the three levels of the first hierarchical mark (capable of passing through), the second hierarchical mark (touchable), and the third hierarchical mark (untouchable) for planning the anti-collision guiding path, if it is possible to plan the reasonable guiding path under this level, the guiding path is adopted to guide the operation end effector to move, in case of the existence of the guiding path, the operation end effector is controlled to move at a third speed being lower than the first speed or the second speed, if it is not possible to plan the reasonable guiding path under this level, the doctor is advised or prompted to manually operate for guiding the operation end to move.

In other words, in case of multiple levels of hierarchical marks, it will give preference to consider of planning the path where the obstacles are without colliding, and then the planning of the path where the obstacles are possible to collide or impossible to pass through is considered, and the planning of the path where the obstacles are possible to collide and pass through is considered at last.

In some embodiments, if the planned guiding path for an anti-collision is unable to avoid generating a touch (including pass through), the vision field of the image end effector can be automatically adjusted for making the operation end effector and/or the corresponding obstacles to be located within the vision field, the doctor is able to observe a collision situation between the operation end effector and the surrounding environment. For example, the vision field of the image end effector can be adjusted by adjusting the camera parameters of the image end effector, and the vision field of the image end effector also can be adjusted by adjusting the position and/or the orientation of the image end effector. Certainly, the vision field of the image end effector also can be adjusted by combining the camera parameters, the position and/or the orientation of the image end effector. Further, a touch range can be acquired from the guiding path, the touch region is a section range where the operation end effector and the corresponding obstacles have a touch relationship, therefore in the touch range the vision field of the operation end effector is adjusted from a start point to an end point of the touch range, and the operation end effector and/or the corresponding obstacles is consistently ensured to be fall within the vision field of the image end effector.

In some embodiments, when there is a touch (including passing through) between the planned guiding path and the obstacles, the operation end effector is controlled to pass through the obstacles by a corresponding passing manner according to the hierarchical marks corresponding to the obstacles, the properties information corresponding to the obstacles, and the type of the operation end effector.

Figure 14:
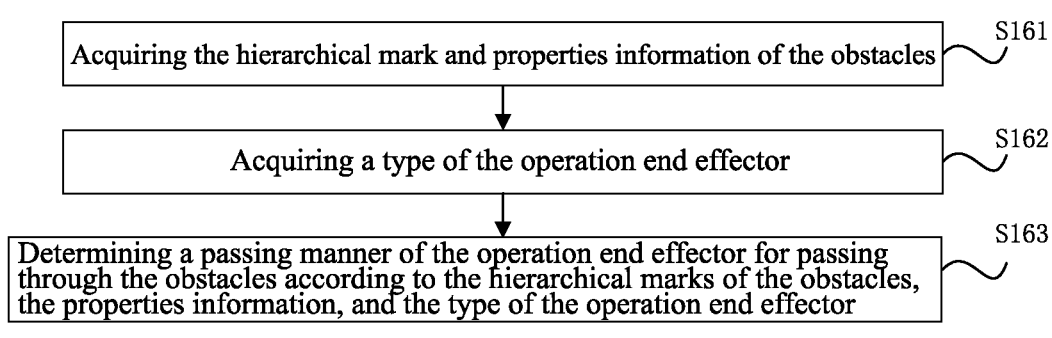

In one embodiment, as shown in FIG. 14, before the step of controlling the operation end effector to pass through the obstacles by a corresponding passing manner according to the hierarchical marks corresponding to the obstacles, the properties information corresponding to the obstacles, and the type of the operation end effector, the method include:

In block S161, acquiring the hierarchical mark and properties information of the obstacles.

The properties information includes a destructible first properties information and an indestructible second properties information, which are stored in the stereoscopic environmental map related to the obstacles. The properties information of the obstacles also can be automatically set by a combination of image identifying and a corresponding relationship table or marked as called; certainly, the properties information of the obstacles also can be manually marked by the doctor, for example, the properties information of the obstacles marked by the doctor are acquired, then the properties information are automatically added to the corresponding obstacles. The properties information also can be stored in the constructed stereoscopic environmental map being related with the corresponding obstacles.

In block S162, acquiring a type of the operation end effector.

The type of the operation end effector can be acquired by image identification, and also can be read from the storing unit of the operating arm. For example. The type of the operation end effector includes a destructible type and an indestructible type.

In block S163, determining a passing manner of the operation end effector for passing through the obstacles according to the hierarchical marks of the obstacles, the properties information of the obstacles, and the type of the operation end effector.

For example, the obstacle has a first hierarchical mark and has the first properties information (capable of being pass through and destructible), and the operation end effector is the operation end effector in the type having destructible function, such as in case of the type of operation end effector to be water jet, plasma knife, ultrasound knife, condensation knife, and electric knife, and the like, the passing manner of passing through the obstacles can be a passing manner of damaging the obstacles for passing the obstacles, this passing manner mainly relies on burning through the obstacles and passing through a burned path for overcoming an obstruction of the obstacles. While controlling the operation end effector to pass through the obstacles in that passing manner, the destructible function is turned on when the operation end reaches the obstacles and is turned off when the operation end effector leaves the obstacles.

For example, in a case of the obstacles having the first hierarchical mark, the second hierarchical mark and/or the second properties information (capable of being passing through, touchable, and/or indestructible), and/or the type of the operation end effector to be indestructible function, the passing manner of passing through the obstacles can be a passing manner of resisting against the obstacles for passing through the obstacles, this passing manner mainly relies on deforming or shifting of the obstacles for overcoming an obstruction of the obstacles.

Figure 15:
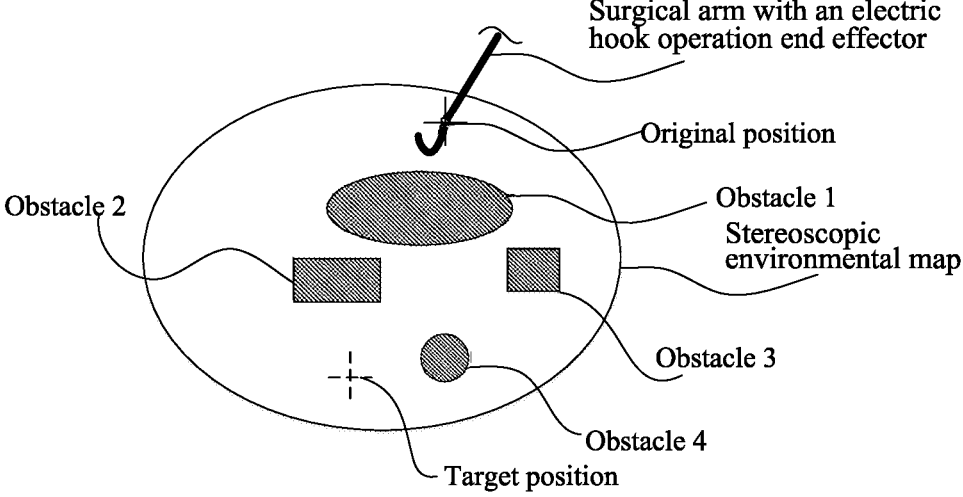
FIGS. 15-16 are schematic diagram views of a stereoscopic environmental map according to an embodiment.
Figure 16:
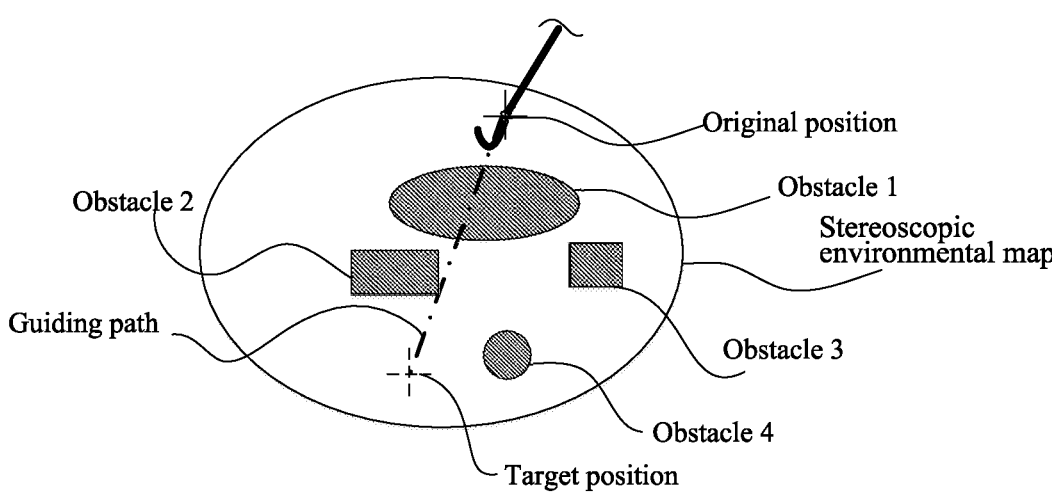

For example, as shown in FIG. 15, supposing there are obstacles 1~4 in the stereoscopic environmental map, the obstacles 1~4 are adipose tissue, liver, kidney, stomach. If the obstacles 1~4 are untouchable, the anti-collision guiding path is unable to be planned. Thus, the obstacles 1~4 are being classified and marked. Supposing the obstacles 1~4 are divided into two levels, for example, the obstacle 1 is divided as the first hierarchical mark (touchable), and the obstacles 2~4 are divided as the second hierarchical mark (untouchable), the effective guiding path is unable to planned even through the obstacle 1 is touched. In the embodiment as shown in FIG. 14, the type of the operation end effector is destructible, thus it can be considered to reclassify and remark the obstacles 1~4, for example, the obstacle 1 is divided as the first hierarchical mark (capable of being passing through and touchable), the obstacle 2 is divided as the second hierarchical mark (touchable), and the obstacles 3~4 are divided as the second hierarchical mark (untouchable). The effective guiding path can be planned from the original position to the target position, the guiding path passes through the obstacle 1, touches the obstacle 2, and is able to avoid the obstacles 3 and 4 at the same time, as shown in FIG. 16. Further, the destructible function is turned on when the operation end effector in an electric hook type moves along the guiding path as shown in FIG. 16 to reach the obstacle 1, and is turned off when passing through the obstacle 1, then the operation end effector resists against the obstacle 2 and passes by the obstacle 2, finally the operation end effector arrives the target position.

In the first guiding mode, the guiding paths generally are different from each other corresponding to the plurality of operation end effectors. According to configuration, the operation end effectors may be guided in turn and moved along the corresponding guiding path to the corresponding target position, may also be guided simultaneously and moved along the corresponding guiding path to the corresponding target position. Certainly, while planning the corresponding guiding path of the operation end effectors, the operation end effectors can be considered as the obstacles in the stereoscopic environmental map, thus the guiding path is properly planned.

In one embodiment, when the guiding mode acquired is the second guiding mode, as shown in FIG. 17, before the block S13, that is the step of generating the guiding path extended from the original position to the target position according to the vision field of the image end effector, the method further includes:

In block S171, determining whether the operation end effector is located within the vision field of the image end effector.

When the operation end effector is not located within the vision field of the image end effector, the block S172 is entered; when the operation end effector is located within the vision field of the image end effector, the block S13 is entered.

In block S172, adjusting the vision field of the image end effector for making the operation end effector to be located within the vision field of the image end effector.

With respect to the block S171, there are several ways to determine whether the operation end effector is located within the vision field of the image end effector, the present disclosure illustrates two ways for implementing the block S171.

In one embodiment, as shown in FIG. 18, the block S171 can include:

In block S1711, acquiring an operation image in the vision field of the image end effector.

In block S1712, determining whether the operation end effector is located within the vision field of the image end effector by identifying whether the operation end effector is located within the operation image by the image identifying.

In the block S1712, if it is recognized that the operation end effector is existed in the operation image, it is determined that the operation end effector is located within the vision field of the image end effector; if it is identified that the operation end effector is not existed in the operation image, it is determined that the operation end effector is not located within the vision field of the image end effector.

To better identify image, the neural network is trained for identifying image. For example, the trained neural network can be convolutional neural network.

In another embodiment, as shown in FIG. 19, the block S171 also can include:

In block S1711', acquiring a current position of the operation end effector.

The current position of the operation end effector is acquired by combining the kinematic model of surgical arm and the joint variables of each of the joint assemblies of the surgical arm to be calculated using forward kinematic, as an example. These joint variables can be detected by the sensors at the corresponding joint assemblies. In other embodiments, the current position of the operation end effector is firstly scanned and identified by adjusting the stereoscopic vision image end effector, for example, by identifying the position of the operation end effector being relative to the image end effector, the current position of the operation end effector in the reference coordinate system is determined by converting the coordinate system.

In block S1712', converting the vision field of the image end effector into a position range.

The vision field is a region, which actually has a boundary, therefore it can be converted into the position range of the reference coordinate, for example.

In block S1713', determining whether the operation end effector is located within the vision field of the image end effector by determining whether the current position is located within the position range.

In the block S1713', if the current position of the operation end effector is located within the position range corresponding to the vision field of the image end effector, it is determined that the operation end effector is located within the vision field of the image end effector; if the current position of the operation end effector is not located within the position range corresponding to the vision field of the image end effector, it is determined that the operation end effector is not located within the vision field of the image end effector.

In some embodiments, the two ways can be combined with each other for mutual verifying whether the operation end effector is located within the vision field of the image end effector. For example, when the result determined by image identification is different from the result determined by the position detection, for safety, the adjustment of the vision field of the image end effector can be stopped, and the adjustment of the vision field of the image end effector is continued when acquiring a confirmation instruction of the doctor. The process also can be used to calibrate the neural network of image identification for improving an accuracy of determination.

The above block S172, that is the step of adjusting the vision field of the image end effector for making the operation end effector to be located within the vision field of the image end effector, also can be implemented in different ways.

Figure 20:
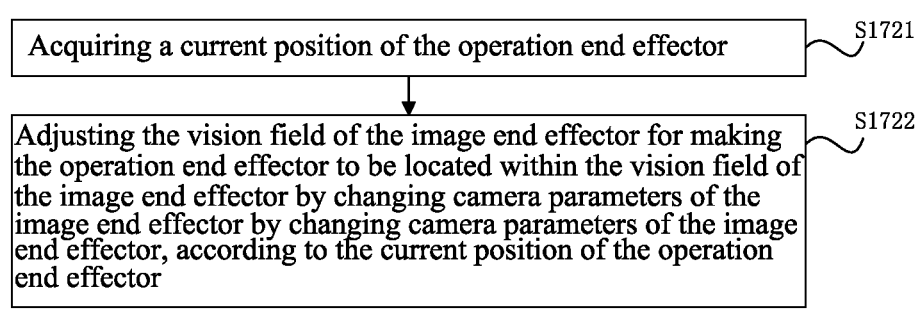

In one embodiment, as shown in FIG. 20, the block S172 can include:

In block S1721, acquiring a current position of the operation end effector.

In block S1722, adjusting the vision field of the image end effector for making the operation end effector to be located within the vision field of the image end effector by changing camera parameters of the image end effector, according to the current position of the operation end effector.

The camera parameters include a field angle and/or a depth of field. If the current position of the operation end effector and the target position can be covered by adjusting the camera parameters being pre-calculated, this way can be adopted, for maintaining the pose of the image end effector.

Figure 21:
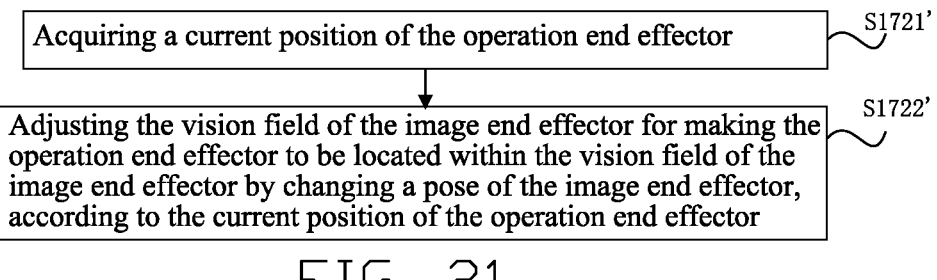

In another embodiment, as shown in FIG. 21, the block S172 also can include:

In block S1721', acquiring a current position of the operation end effector.

In block S1722', adjusting the vision field of the image end effector for making the operation end effector to be located within the vision field of the image end effector by changing a pose of the image end effector, according to the current position of the operation end effector.

The pose includes a position and/or an orientation. If a region between the current position of the operation end effector and the target position can be covered by adjusting the pose of the image end effector being pre-calculated, this way can be adopted, for maintaining the camera parameters of the image end effector.

Figure 22:
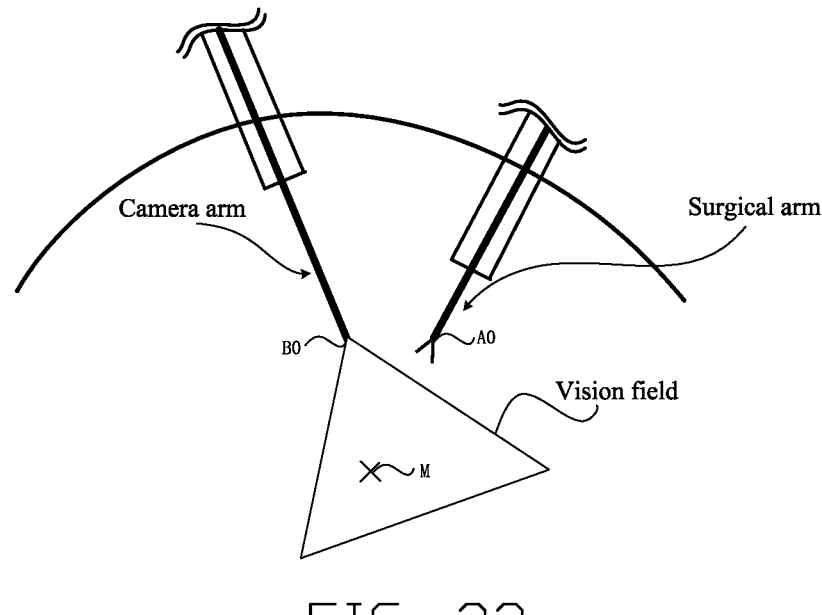
Figure 23:
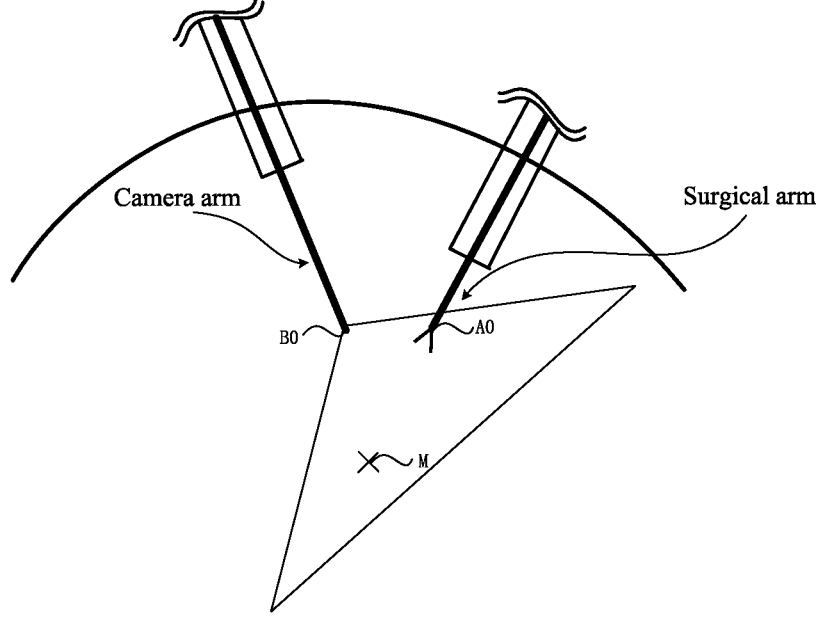
Figure 24:
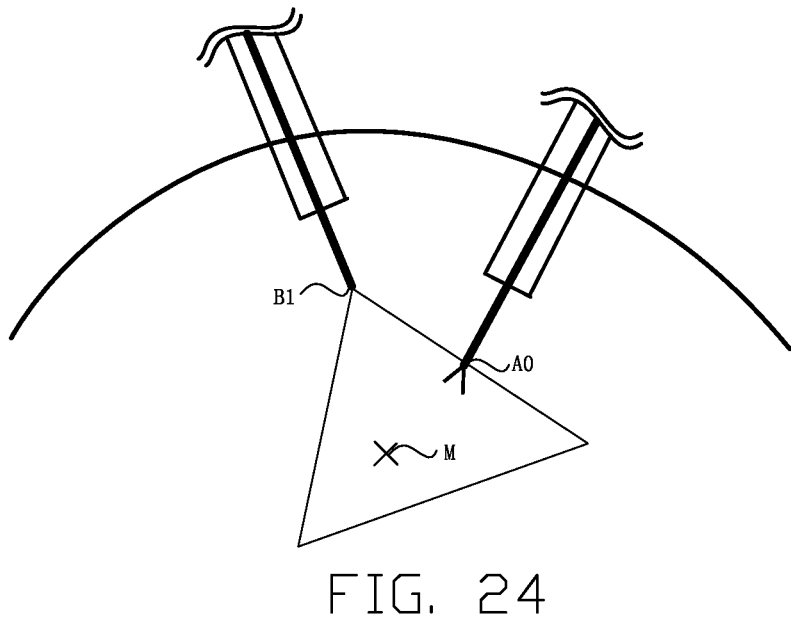

Take the multi-port surgical robot as an example, referring to FIGS. 22 to 24. Supposing as shown in FIG. 22, the current position of the image end effector of the camera arm is B0, the current position of the operation end effector of the surgical arm is A0, the vision field of B0 is the target vision field, A0 is located besides the target vision field. In one embodiment, as shown in FIG. 23, the current position of the image end effector B0 remains constant, the vision field is adjusted by adjusting the camera parameters, such as the vision angle, for making A0 to be located within the vision field after adjusted. In one embodiment, as shown in FIG.

24, the camera parameters of the image end effector remain constant, the vision field is adjusted by adjusting the pose, such as the position, of the image end effector to be B1, for making A0 to be located within the vision field after adjusted.

Figure 25:
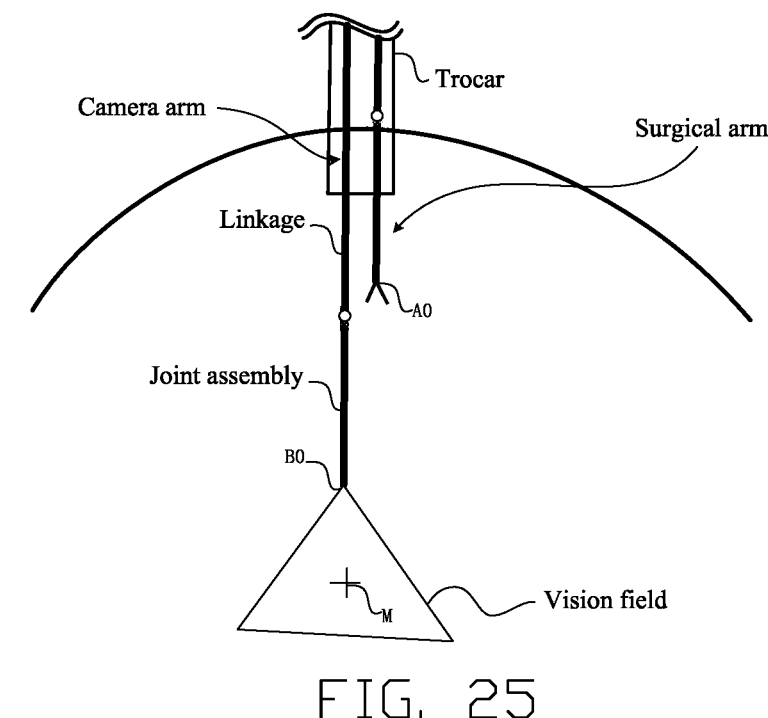

Certainly, it is also suitable for the single-port surgical robot, referring to FIGS. 25 to 27. Supposing as shown in FIG. 25, the current position of the image end effector of the camera arm is B0, the current position of the operation end effector of the surgical arm is A0, the vision field of B0 is the target vision field, A0 is located besides the target vision field. In one embodiment, as shown in FIG. 26, the camera parameters of the image end effector remain constant, the vision field is adjusted by adjusting the pose, such as the position, of the image end effector to be B1, for making A0 to be located within the vision field after adjusted; as shown in FIG. 27, similarly, the camera parameters of the image end effector remain constant, the vision field is adjusted by adjusting the pose of the image end effector to be B1, for making A0 to be located within the vision field after adjusted. Certainly, in some situations, the current position of the image end effector B0 remains constant, the vision field is adjusted by adjusting the camera parameters, such as the field angle, for making A0 to be located within the vision field after adjusted, which is not shown in the figure.

In some embodiments, the two ways can be combined for adjusting the vision field of the image end effector together to better move towards the current position and/or the target position for making the current position and/or the target position to be located within the vision field of the image end effector. For example, the pose of the image end effector is adjusted in priority; another example, the camera parameters of the image end effector are adjusted in priority. The object being adjusted in priority (the pose and camera parameters of the image end effector) can be configured by an instruction inputted by the doctor. For example, when the pose of the image end effector is adjusted in priority, the pose of the image end effector is adjusted as possible for making the vision field to move to the current position and/or the target position, if the movement reaches a limit, the vision field of the image end effector does not cover the current position of the image end effector and/or the target position, the camera parameters of the image end effector are adjusted as assisted for making the vision field to cover the current position of the image end effector and/or the target position. When the camera parameters of the image end effector are adjusted in priority, the camera parameters of the image end effector are adjusted as possible for making the vision field to move to the current position and/or the target position, if the movement reaches a limit, the vision field of the image end effector does not cover the current position of the image end effector and/or the target position, the pose of the image end effector is adjusted as assisted for making the vision field to cover the current position of the image end effector and/or the target position.

In some embodiments, even only the pose of the image end effector is adjusted, priorities also can be set, for example, the orientation is adjusted in priority; another example, the position is adjusted in priority. Similarity, even only the camera parameters of the image end effector are adjusted, priorities also can be set, for example, the field angle is adjusted in priority; another example, the depth of the field is adjusted in priority. The object being adjusted in priority (the orientation and the position in the pose, and/or the field angle and the depth of the vision in the camera parameters) also can be configured according to an instruction inputted by the doctor.

In some embodiments, a plurality of levels of the priority are configured for adjusting the vision field of the image end effector, and corresponding parameters of the image end effector are adjusted step by step according to the configured priorities for achieving an adjustment of the vision field, until the vision field can cover the current position of the image end effector and/or the target position. For example, a first level of the priority is adjusting the pose of the image end effector, a second level of the priority is adjusting the orientation in the pose of the image end effector, a third level of the priority is adjusting the field angle of the camera parameters of the image end effector. Assuming combining the adjustments to the pose and the camera parameters of the image end effector can make the vision filed of the image end effector to be able to cover the current position and/or the target position of the operation end effector, the whole work process can be:

The orientation of the image end effector is firstly adjusted to be a reachable limit of the vision field;

If the current vision can cover the current position of the operation end effector and/or the target position, the adjustment is accomplished; if the current vision fails to cover the current position of the operation end effector and/or the target position, the position of the image end effector is adjusted to reach a reachable limit of the vision field;

If the current vision can cover the current position of the operation end effector and/or the target position, the adjustment is accomplished; if the current vision still fails to cover the current position of the operation end effector and/or the target position, the field angle of the image end effector is adjusted to reach a reachable limit of the vision field;

If the current vision can cover the current position of the operation end effector and/or the target position, the adjustment is accomplished; if the current vision still fails to cover the current position of the operation end effector and/or the target position, the depth of field of the image end effector is adjusted to reach a reachable limit of the vision field, the vision field should be able to cover the current position of the operation end effector and/or the target position.

Under the second guiding mode, as shown in FIG. 28, the above block S13, that is the step of generating the guiding path extended from the original position to the target position, includes:

In block S181, acquiring a current position of the operation end effector in real time, and initializing the current position as the original position.

In block S182, generating the guiding path extended from the current position to the target position according to the vision field of the image end effector, and the guiding path is located within the vision field of the image end effector.

Preferably, in the above block S182, the guiding path extended from the current position to the target position is generated by planning the anti-collision path according to the vision field of the image end effector. The anti-collision path is planned in the local vision field in here, which can refer the foregoing method of planning the anti-collision path. Details are not described herein again.

In one embodiment, under the second guiding mode, the method further includes: constraining the adjustment to the vision filed of the image end effector consistently to be under a condition of the operation end effector to be located within the vision field of the image end effector. For example, when the image end effector is outside the vision field of the image end effector, it can be considered to generate a resistance force for blocking the movement of the operation end effector in corresponding degree of freedom.

In one embodiment, under the second guiding mode, the vision fields of the image end effector in adjacent time points are a first vision field and a second vision field, there is an overlapped region between the first vision field and the second vision field, the operation end effector is limited to move to the target position by passing through the overlapped region.

In one embodiment, under the second guiding mode, the method further includes: constraining the vision field of the image end effector to only move towards to a direction of the target position where the operation end effector is expected to reach. The constraining can avoid or prevent the vision field of the image end effector to be adjusted ineffectively being unrelated with the purpose of the movement of which towards to the target position.

In one embodiment, under the second guiding mode, the method further includes: forbidding the operation end effector to be moved when the operation end effector is not located within the vision field of the image end effector. The operation end effector can be prevented from to be outside the vision field of the image end effector, therefore the safety can be further ensured.

In one embodiment, under the second guiding mode, the method further includes: detecting whether a start instruction is acquired; when the start instruction is acquired, determining whether the operation end effector is located within the vision field of the image end effector.

The start instruction is triggered to generate when the surgical arm is mounted on the power mechanism, and is triggered after the surgical arm is mounted on the power mechanism by the confirmed instruction inputted by the doctor, but not being limited. For example, the sensor, such as the distance sensor, is mounted on the power mechanism, when the surgical arm is mounted on the power mechanism, the sensor detects a distance between the surgical arm and the power mechanism, the start instruction is triggered to generate when the controller determines that the distance is less than or equal to a default value.

In some embodiments, as shown in FIG. 29, the method further includes:

In block S191, determining whether a current vision field of the image end effector is an original vision field, when the operation end effector basically moves from the original position to the target position.

The original vision is the vision field of the image end effector at a previous time point before being firstly adjusted.

In block S192, adjusting the current vision field of the image end effector to be the original vision field, when the current vision field of the image end effector is not the original vision field.

In one embodiment, before the block S192, that is the step of adjusting the current vision field of the image end effector to be the original vision field, the method further includes: acquiring and recording camera parameters and a pose corresponding to the original vision field determined by the image end effector. Further, in the block S192, that is in the step adjusting the current vision field of the image end effector to be the original vision field, the method further includes: directly restoring the current vision field of the image end effector to the original vision field according to the recorded camera parameters and the pose corresponding to the original vision field determined by the image end effector.

In one embodiment, a computer readable storage medium is provided. The computer readable storage medium stores computer programs, the computer programs is configured to load and execute by a processor to implement the following steps: acquiring an original position of an operation end effector; acquiring a target position of the operation end effector where the operation end effector is expected to reach; generating a guiding path extended from the original position to the target position according to a vision field of the image end effector; adjusting the operation end effector to move along the guiding path from the original position to the target position.

Figure 30:
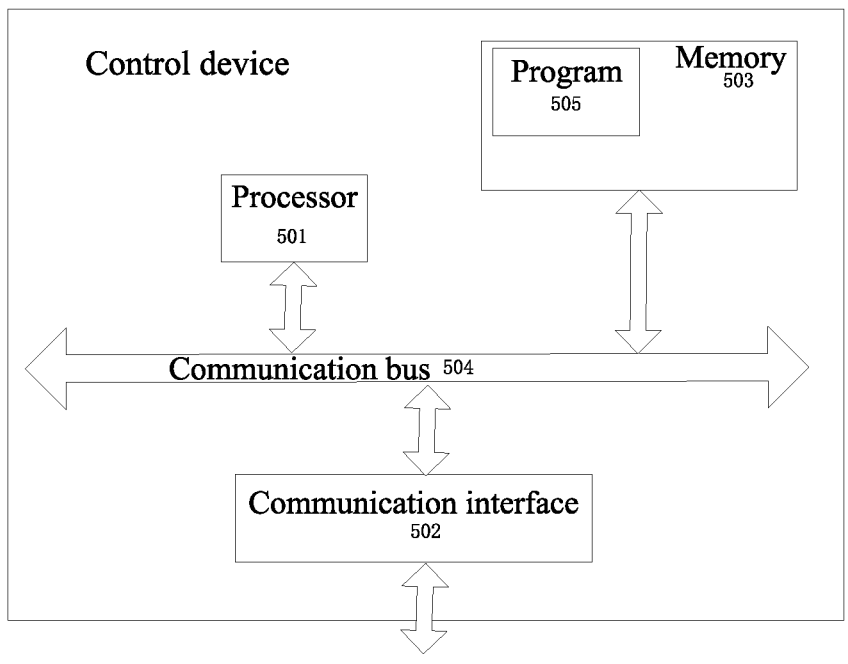
FIG. 30 is schematic diagram view of a structure of a control device of a surgical robot according to an embodiment of the present disclosure.

In one embodiment, a control device of a surgical robot is provided. As shown in FIG. 30, the control device can include: a processor 501, a communication interface 502, a memory 503, and a communication bus 504.

The processor 501, the communication interface 502, and the memory 503 can communicate with each other by the communication bus 504.

The communication interface 502 is configured to communicate with network element(s), for example various sensor(s) or motor(s) or solenoid valve(s) or other client(s) or server(s).

The processor 501 is configured for loading and executing the computer program 505 to carry out the method described in any of the above embodiments.

The program 505 may include program codes including computer operation instructions.

The processor 501 may be a central processing unit (CPU), an Application Specific Integrated Circuit (ASIC), one or more integrated circuits configured to implement one or more of the embodiments of the present disclosure, or a Graphics Processing Unit (GPU). The control device can include at least one processor. Each processor can be the same type of processors, such as one or more CPUs, or one or more GPUs; each processor can also be different types of processors, such as one or more CPUs and One or more GPUs.

The memory 503 is configured to store the program 505. The memory 503 may be a high-speed read-only memory, and may also be a non-volatile memory, such as at least one disk memory.

The program 505 can specifically be configured to make the processor 501 perform the following operations: acquiring an original position of an operation end effector; acquiring a target position of the operation end effector where the operation end effector is expected to reach; generating a guiding path extended from the original position to the target position according to a vision field of the image end effector; adjusting the operation end effector to move along the guiding path from the original position to the target position.

Various technical features of the above-described embodiments may be combined in any combination, so that the description is concise, and all possible combinations of the various technical features in the above-described embodiments are described. However, as long as the combination of these technical features does not conflict, it is to be understood that the scope of the present specification is not to be taken in a limiting sense.

The above-described embodiments have only expressed several embodiments of the present disclosure, which are described in more detail and detail, but are not therefore to be construed as limiting the scope of the present disclosure. It should be noted that variations and modifications may be made to one of ordinary skill in the art without departing from the spirit of the present disclosure, all of which fall within the scope of the present disclosure. Therefore, the scope of the appended claims should be accorded the broadest interpretation so as to encompass all such modifications and similar arrangements. Therefore, the scope of protection of the patent disclosure should be based on the appended claims.

What is claimed is:

1. A method for guiding a surgical arm to move in a surgical robot, wherein a distal end of the surgical robot comprises a plurality of operating arms, the operating arms comprise a camera arm having an image end effector and a surgical arm having an operation end effector, the method comprises:

acquiring an original position of the operation end effector;

acquiring an operation mode inputted;

determining a target position where the operation end effector is expected to reach according to the operation mode acquired;

generating a guiding path extended from the original position to the target position according to a vision field of the image end effector; and adjusting the operation end effector to move along the guiding path from the original position to the target position;

wherein generating the guiding path extended from the original position to the target position according to the vision field of the image end effector comprises:

acquiring a guiding mode inputted, the guiding mode comprises a first guiding mode and a second guiding mode, the first guiding mode comprises a mode of automatically adjusting the vision field of the image end effector, the second guiding mode comprises a mode of manually adjusting the vision field of the image end effector; and adjusting the vision field of the image end effector according to the guiding mode acquired to generate the guiding path extended from the original position to the target position.

2. The method of claim 1, wherein the operation mode comprises a first operation mode; the first operation mode is used to guide the operation end effector to insert into a first target position in a human body.

3. The method of claim 2, wherein when the operation mode acquired is the first operation mode, determining the target position where the operation end effector is expected to reach according to the operation mode acquired comprises:

acquiring a target vision field of the image end effector; and determining the target position where the operation end effector is expected to reach according to the target vision field.

4. The method of claim 1, wherein the operation mode comprises a second operation mode, the second operation mode is configured to guide the operation end effector to move to a second target position.

5. The method of claim 4, wherein the surgical robot comprises a trocar, a proximal end of the trocar is connected to the distal end of the surgical robot, and a distal end of the trocar is configured to insert and fix at a notch, the trocar is configured to guide the surgical arm to insert into a human body through the notch; when the operation mode acquired is the second operation mode, determining the target position where the operation end effector is expected to reach according to the operation mode acquired comprises:

acquiring a position of a target point related with the trocar as the target position.

6. The method of claim 1, wherein the image end effector is a stereoscopic vision image end effector, when the guiding mode acquired is the first guiding mode, adjusting the vision field of the image end effector according to the guiding mode acquired to generate the guiding path extended from the original position to the target position comprises:

adjusting the vision field of the image end effector for global scanning an environment and constructing a stereoscopic environmental map by using a parallax method; and generating the guiding path covering the original position and the target position according to the stereoscopic environmental map.

7. The method of claim 1, wherein the image end effector is a stereoscopic vision image end effector, when the guiding mode acquired is the first guiding mode, adjusting the vision field of the image end effector according to the guiding mode acquired to generate the guiding path extended from the original position to the target position comprises:

acquiring a reachable region of the vision field of the image end effector;

adjusting the vision field of the image end effector for scanning an environment of the reachable region and constructing a stereoscopic environmental map by using a parallax method; and generating the guiding path covering the original position and the target position according to the stereoscopic environmental map.

8. The method of claim 7, wherein before adjusting the vision field of the image end effector for scanning the environment of the reachable region and constructing the stereoscopic environmental map by using the parallax method, the method further comprises:

determining whether both the original position and the target position are located within the reachable region; and when both the original position and the target position are located within the reachable region, adjusting the vision field of the image end effector for scanning the environment of the reachable region and constructing the stereoscopic environmental map by using the parallax method.

9. The method of claim 1, wherein the image end effector is a stereoscopic vision image end effector, when the guiding mode acquired is the first guiding mode, adjusting the vision field of the image end effector according to the guiding mode acquired to generate the guiding path extended from the original position to the target position comprises:

acquiring a reachable region of the operation end effector;

adjusting the vision field of the image end effector for at least scanning a local environment of the reachable region containing the original position and the target position and constructing a stereoscopic environmental map by using a parallax method; and generating the guiding path covering the original position and the target position according to the stereoscopic environmental map.

10. The method of claim 6, wherein the surgical robot comprises a display, the method further comprises:

displaying the stereoscopic environmental map in the display; and displaying the position of the operation end effector in the stereoscopic environmental map in real time.

11. The method of claim 6, wherein generating the guiding path covering the original position and the target position according to the stereoscopic environmental map comprises:

planning an anti-collision path according to the stereoscopic environmental map for generating the guiding path covering the original position and the target position.

12. The method of claim 11, wherein constructing the stereoscopic environmental map comprises:

identifying obstacles within the vision field of the image end effector;

acquiring hierarchical marks for the obstacles; and constructing the stereoscopic environmental map containing the hierarchical marks corresponding to each of the obstacles.

13. The method of claim 12, wherein acquiring hierarchical marks for the obstacles comprises:

acquiring the hierarchical marks corresponding to the obstacles from a default relationship table according to types of the obstacles identified; and/or receiving the hierarchical marks inputted corresponding to the obstacles.

14. The method of claim 12, wherein generating the guiding path covering the original position and the target position according to the stereoscopic environmental map comprises:

planning the anti-collision path according to the stereoscopic environmental map and the hierarchical marks corresponding to the obstacles for generating the guiding path covering the original position and the target position.

15. The method of claim 14, wherein the method further comprises:

when there is no touch relationship between the guiding path and the obstacles, controlling the operation end effector to move at a first speed, and when there is a touch relationship between the guiding path and the obstacles, controlling the operation end effector to move at a second speed lower than the first speed.

16. The method of claim 1, wherein when the guiding mode acquired is the second guiding mode, before generating the guiding path extended from the original position to the target position according to the vision field of the image end effector, the method further comprises:

determining whether the operation end effector is located within the vision field of the image end effector;

when the operation end effector is not located within the vision field of the image end effector, adjusting the vision field of the image end effector for making the operation end effector to be located within the vision field of the image end effector; and when the operation end effector is located within the vision field of the image end effector, generating the guiding path extended from the original position to the target position according to the vision field of the image end effector.

17. The method of claim 16, wherein adjusting the vision field of the image end effector for making the operation end effector to be located within the vision field of the image end effector comprises:

acquiring a current position of the operation end effector; and adjusting the vision field of the image end effector for making the operation end effector to be located within the vision field of the image end effector by changing camera parameters and/or a pose of the image end effector according to the current position of the operation end effector.

18. A computer readable storage medium, comprising:

a storage medium, storing a computer program configured to be loaded and executed by a processor to implement following steps:

acquiring an original position of the operation end effector;

acquiring an operation mode inputted;

determining a target position where the operation end effector is expected to reach according to the operation mode acquired;

generating a guiding path extended from the original position to the target position according to a vision field of an image end effector; and adjusting the operation end effector to move along the guiding path from the original position to the target position;

wherein generating the guiding path extended from the original position to the target position according to the vision field of the image end effector comprises:

acquiring a guiding mode inputted, the guiding mode comprises a first guiding mode and a second guiding mode, the first guiding mode comprises a mode of automatically adjusting the vision field of the image end effector, the second guiding mode comprises a mode of manually adjusting the vision field of the image end effector; and adjusting the vision field of the image end effector according to the guiding mode acquired to generate the guiding path extended from the original position to the target position.

19. A surgical robot, comprising:

operating arms, comprising a camera arm having an image end effector and a surgical arm having an operation end effector; and a controller, the controller is coupled to the operating arms, and is configured to implement following steps:

acquiring an original position of the operation end effector;

acquiring an operation mode inputted;

determining a target position where the operation end effector is expected to reach according to the operation mode acquired;

generating a guiding path extended from the original position to the target position according to a vision field of the image end effector; and adjusting the operation end effector to move along the guiding path from the original position to the target position;

wherein generating the guiding path extended from the original position to the target position according to the vision field of the image end effector comprises:

acquiring a guiding mode inputted, the guiding mode comprises a first guiding mode and a second guiding mode, the first guiding mode comprises a mode of automatically adjusting the vision field of the image end effector, the second guiding mode comprises a mode of manually adjusting the vision field of the image end effector; and adjusting the vision field of the image end effector according to the guiding mode acquired to generate the guiding path extended from the original position to the target position.

\* \* \* \* \*